(12) United States Patent
Romano et al.

(10) Patent No.: US 7,329,250 B2
(45) Date of Patent: Feb. 12, 2008

(54) METHOD AND APPARATUS FOR CONVERTING SUPPLIES AND REDUCING WASTE

(75) Inventors: Jack W. Romano, Kirkland, WA (US); Adam L. Smith, Seattle, WA (US)

(73) Assignee: Medindica - Pak, Inc., Kirkland, WA (US)

( * ) Notice: Subject to any disclaimer, the term of this patent is extended or adjusted under 35 U.S.C. 154(b) by 0 days.

(21) Appl. No.: 10/730,297

(22) Filed: Dec. 8, 2003

(65) Prior Publication Data

US 2004/0122383 A1   Jun. 24, 2004

Related U.S. Application Data

(60) Provisional application No. 60/432,517, filed on Dec. 11, 2002.

(51) Int. Cl.
 *A61M 1/00* (2006.01)
 *B67C 3/00* (2006.01)
 *B65B 3/04* (2006.01)
 *A61B 19/00* (2006.01)

(52) U.S. Cl. .................. 604/540; 141/18; 604/317; 604/403

(58) Field of Classification Search ........ 604/317–328, 604/6.15, 35, 354, 403–416, 540, 541, 543; 141/18–29; 206/829
See application file for complete search history.

(56) References Cited

U.S. PATENT DOCUMENTS

| 3,381,687 | A | * | 5/1968 | Andersen et al. ............ 604/321 |
| 3,556,101 | A | * | 1/1971 | Economou ................... 604/319 |
| 3,648,698 | A | * | 3/1972 | Doherty ....................... 604/319 |
| 3,699,815 | A |   | 10/1972 | Holbrook |
| 3,773,211 | A | * | 11/1973 | Bridgman .............. 220/495.06 |
| 3,782,414 | A |   | 1/1974 | Holbrook |
| 3,915,189 | A |   | 10/1975 | Holbrook |
| 3,929,937 | A | * | 12/1975 | Clendinning et al. ....... 525/190 |
| RE29,321 | E |   | 7/1977 | Holbrook |
| 4,178,976 | A | * | 12/1979 | Weiler et al. ................ 604/415 |
| 4,180,722 | A | * | 12/1979 | Clewans ..................... 219/502 |
| 4,228,798 | A |   | 10/1980 | Deaton |
| 4,245,637 | A |   | 1/1981 | Nichols |
| 4,306,557 | A |   | 12/1981 | North |
| 4,321,922 | A |   | 3/1982 | Deaton |
| 4,347,946 | A |   | 9/1982 | Nichols |
| 4,384,580 | A |   | 5/1983 | Leviton |
| 4,388,922 | A |   | 6/1983 | Telang |
| 4,419,093 | A |   | 12/1983 | Deaton |
| 4,460,361 | A |   | 7/1984 | Nichols |

(Continued)

FOREIGN PATENT DOCUMENTS

WO    WO 01/87223 A1  *  11/2001

(Continued)

*Primary Examiner*—Tatyana Zalukaeva
*Assistant Examiner*—Michael G Bogart

(57) ABSTRACT

A method and apparatus for technique and cycling (Technicycling as herein defined) such that converting delivery supply containers (supplies) into waste and disposal receptacles is disclosed. More particularly, a container transformation comprising deriving a supply container from a health care delivery sequence and converting the container into a waste receptacle by connection to a vacuum/suction source and collection system reduces the amount of waste contributed to the waste stream.

27 Claims, 19 Drawing Sheets

U.S. PATENT DOCUMENTS

| | | |
|---|---|---|
| 4,516,973 A | 5/1985 | Telang |
| 4,620,846 A * | 11/1986 | Goldberg et al. .............. 604/28 |
| 4,846,800 A * | 7/1989 | Ouriel et al. .............. 604/6.15 |
| 4,870,975 A | 10/1989 | Cronk |
| 4,976,707 A * | 12/1990 | Bodicky et al. ............ 604/408 |
| 5,045,074 A * | 9/1991 | Satterfield et al. .......... 604/317 |
| 5,049,273 A | 9/1991 | Knox |
| 5,192,439 A * | 3/1993 | Roth et al. .................. 210/485 |
| 5,254,080 A | 10/1993 | Lindsay |
| 5,269,924 A * | 12/1993 | Rochat ....................... 210/445 |
| 5,288,290 A * | 2/1994 | Brody ......................... 604/32 |
| 5,318,510 A * | 6/1994 | Cathcart ................... 604/6.09 |
| 5,470,324 A | 11/1995 | Cook |
| 5,624,417 A | 4/1997 | Cook |
| 5,637,103 A | 6/1997 | Kerwin |
| 5,637,104 A | 6/1997 | Ball |
| 5,683,371 A | 11/1997 | Hand |
| 5,725,516 A | 3/1998 | Cook |
| 5,792,126 A | 8/1998 | Tribastone |
| 5,827,246 A * | 10/1998 | Bowen ....................... 604/313 |
| 5,901,717 A | 5/1999 | Dunn |
| 5,960,837 A | 10/1999 | Cude |
| 6,071,095 A * | 6/2000 | Verkaart ................... 417/477.9 |
| 6,152,902 A | 11/2000 | Christian |
| 6,159,416 A * | 12/2000 | Kawakami et al. ......... 264/531 |
| 6,387,070 B1 * | 5/2002 | Marino et al. ................ 604/35 |
| 6,635,028 B1 | 10/2003 | Ielpo |
| 6,907,879 B2 * | 6/2005 | Drinan et al. .......... 128/202.22 |
| 2001/0037069 A1 | 11/2001 | Carlson et al. |
| 2003/0079803 A1 | 5/2003 | Romano |
| 2003/0132249 A1 | 7/2003 | Romano |

FOREIGN PATENT DOCUMENTS

WO     WO 2004/052730 A3 *   6/2004

* cited by examiner

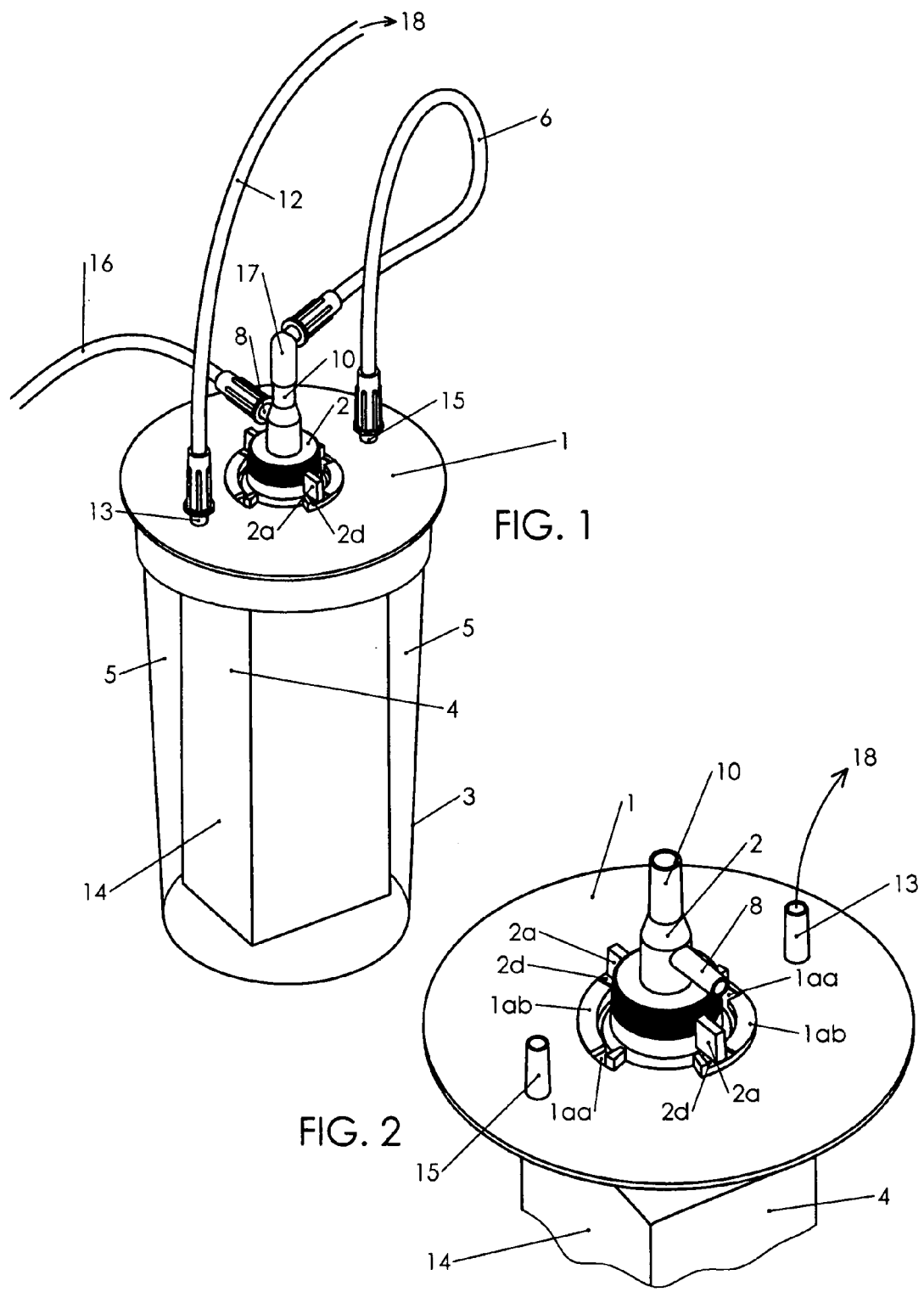

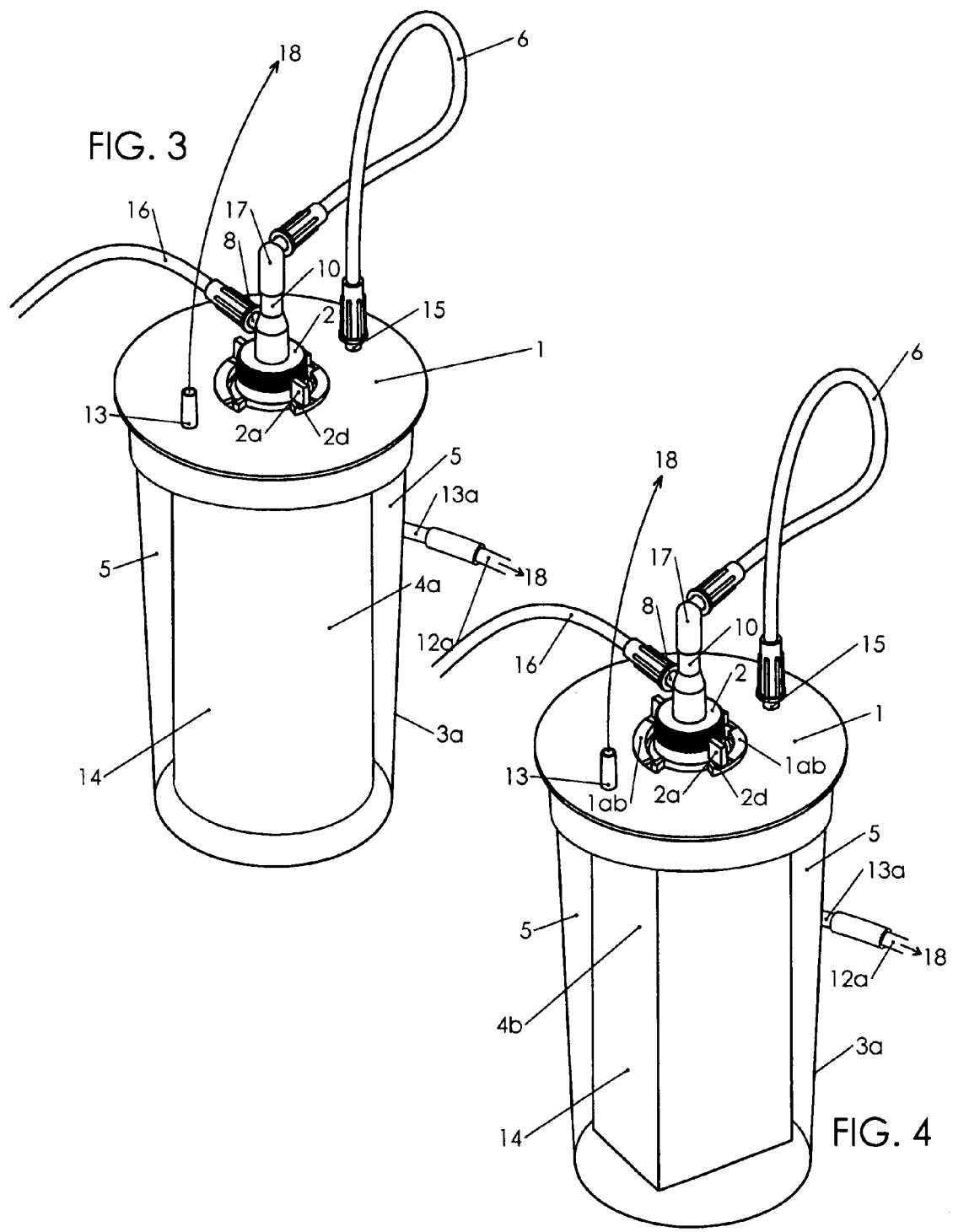

SECTION A-A

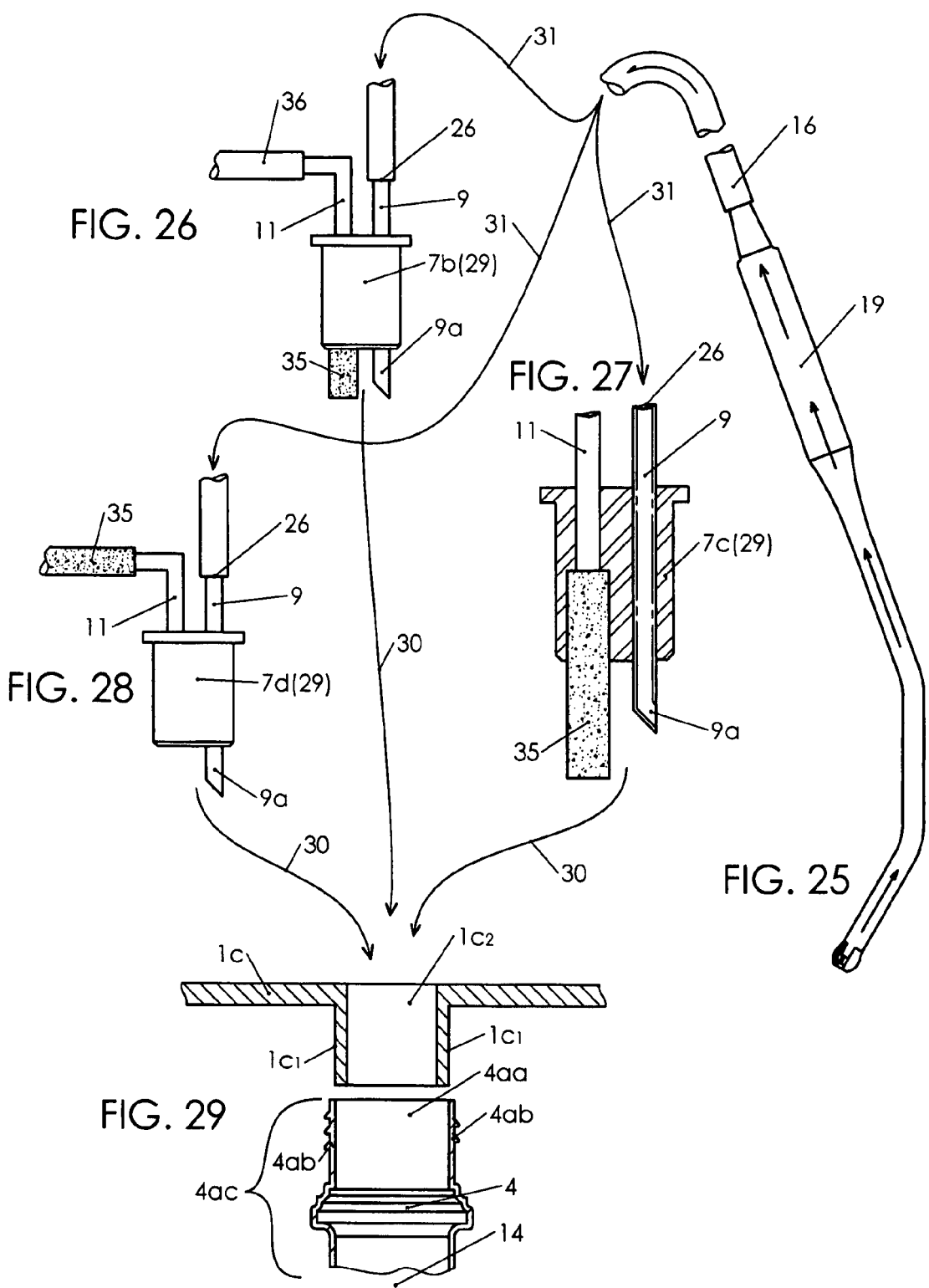

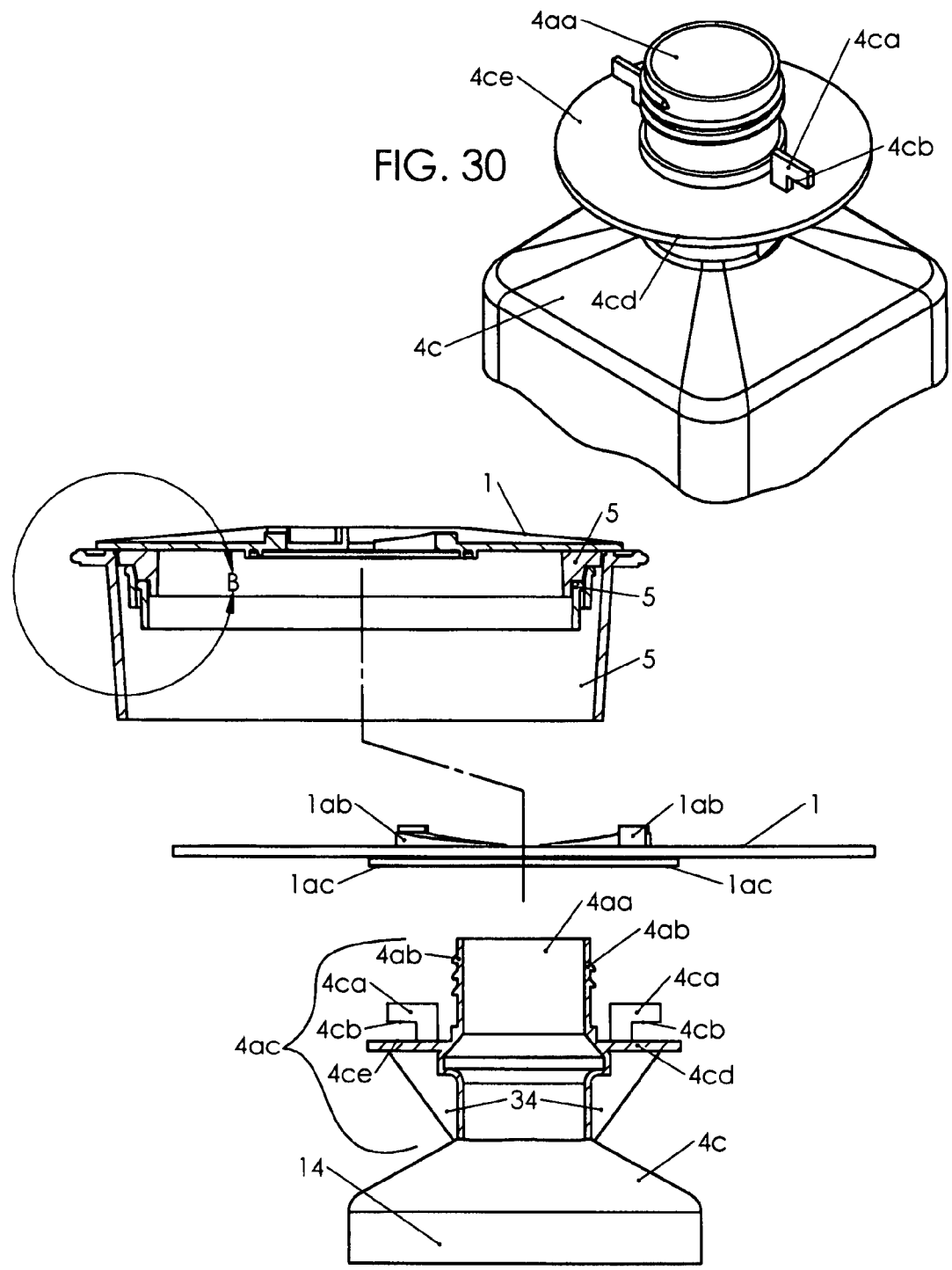

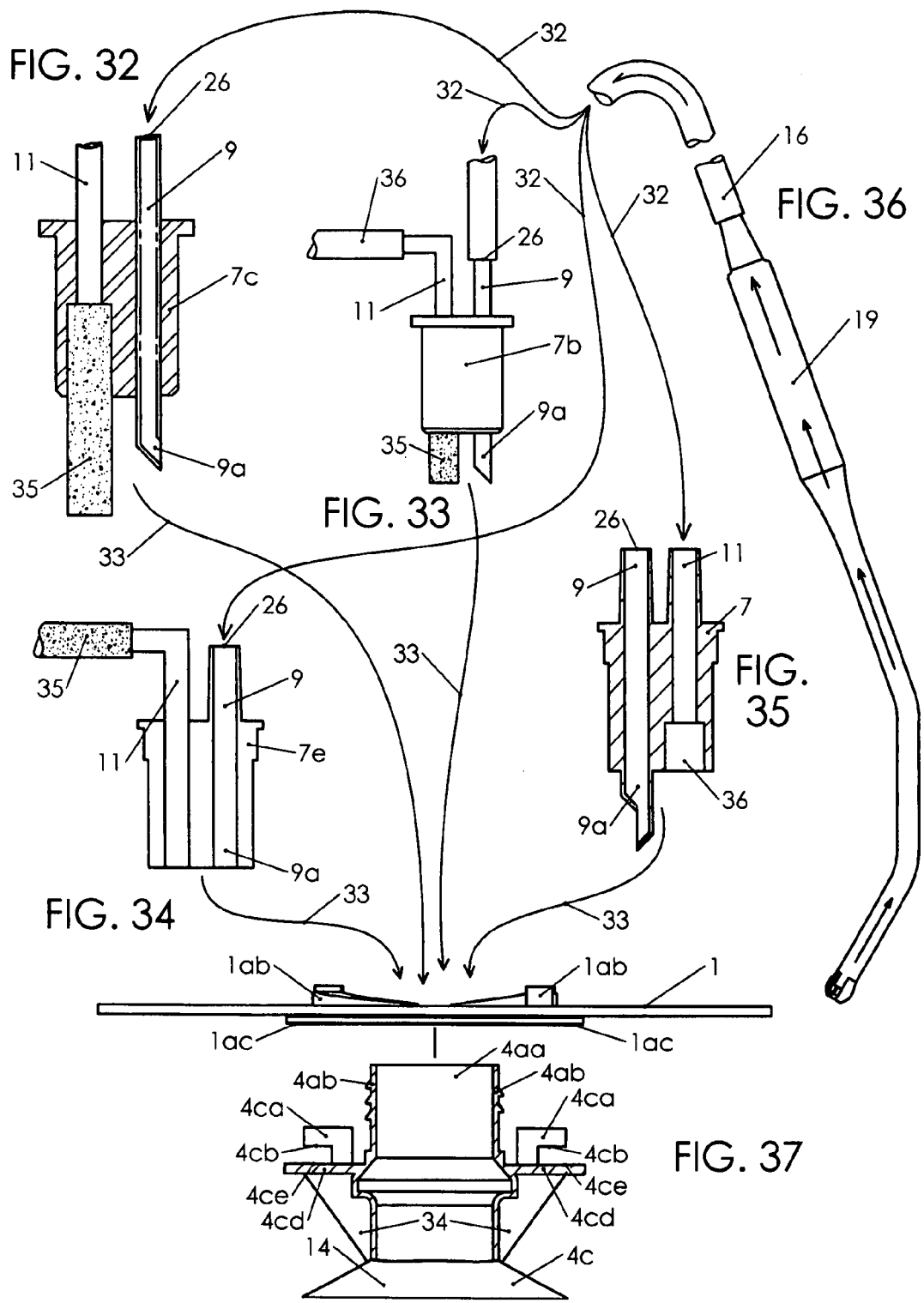

METHOD AND APPARATUS FOR CONVERTING SUPPLIES AND REDUCING WASTE

CROSS REFERENCE TO RELATED APPLICATION

This application claims the benefit, under 35 U.S.C. 119(e) of U.S. Provisional Patent Application Ser. No. 60/432,517, filed Dec. 11, 2002.

FIELD OF THE INVENTION

This invention(s) relates to the field of reducing the waste stream burden in the medical field.

BACKGROUND OF THE INVENTION

In particular, this application relates to systems used for the collection and disposal of certain medical waste. The collection of fluent waste material is a common procedure in the medical field. Most methods of surgical waste collection are carried out using vacuum suction. Some methods use gravity, while some use impelling devices which produce suction/vacuum. Examples of such impelling devices may comprise a meniscus shaver, a lipo-suction system, an arthroscopic fluid pump, an endoscopic irrigation and aspiration wand and the like. Surgical fluid waste is collected in containers commonly referred to as canisters, and or canister liners. These waste collection devices are generally disposable, some are recycled reprocessed or re-washed. Some collection devices are reused. Some are partially reused, while some are intermittently reused. Some are disposable or partially disposable. Some are used in conjunction with servicing units while some are used with additive agents for treating the waste material. Some are used multiple times on multiple patients without preferable cleaning between patients. In certain instances, reused devices are cleaned, reprocessed, sterilized, re-sterilized, and/or re-cycled and prepared for re-use. There are disadvantages to the use of disposable collection canisters and canister liners. One problem is that disposable collection canisters and disposable collection liners contribute contaminated infections plastic waste to the medical waste stream which is undesirable for the environment. Re-use of disposable collection devices by re-cleaning or re-processing re-cycling and/or sterilizing, has the disadvantages of adding costly labor, and requiring additional labor costs for sorting, containing, transporting and handling of contaminated medical waste canisters, and then the added costs of product re-entry into the cleaning and re-sterilization internal systems. There is a significant need to reduce medical waste. The need to reduce medical waste is a serious common goal of the US Environmental Protection Agency, and the American Hospital Association which has entered into a landmark "Memorandum of Understanding" formally establishing the goals to reduce medical waste 50% by the year 2010. Hospitals for Healthy Environment (www.h2e-online.org) is the name of the aforementioned alliance and is supported by many formidable organizations and companies such as the American Nurses Association, Health Care Without Harm, Group Purchasing Organizations, Health Care Systems, State and local government agencies, Health Care Associations and the like.

DESCRIPTION OF THE RELATED ART

Certain disadvantages of the prior art in these regards will become better understood by explanation of these following references. U.S. Pat. No. 5,792,126 to Tribastone et. al., discloses a collection canister system comprising canister interiors of preferably 5,000, 10,000 and 15,000 cubic centimeters and are taught to be effective for all procedures. A container of this size has disadvantages because it is too big for many collection applications. For example, suction collection for anesthesia, whereby it is convenient to have a small collection canister attached to an anesthesia machine is preferable, especially in that most anesthesia suction volumes constitute just a few cubic centimeters of sputum or pharangeal/throat saliva most of the time. Larger equipment is also inconvenient in smaller rooms, where suction collection equipment is found such as the emergency room, intensive care units in patient hospital rooms, coronary care units, and neo-natal and infant care units, physician offices, physician owned surgery suites, out patient surgery centers, ambulances, and other rooms defining smaller confined spaces. There are also concerns with cross contamination in any system where contaminated waste material remains in a room/location during the presence of multiple patients. This problem is most prevalent in intensive care and other patient units where the most sick patients are treated. Another disadvantage of 5,000, 10,000 and 15,000 cubic centimeter containers is weight. Such weight in these very heavy volumes provide for extremely difficult ergonomics and handling problems posing significant risk to personnel, such as back, neck, and upper extremity injuries. Another disadvantage of such large and heavy containers is its size. Such large containers are more difficult to clean and cumbersome to handle and because the awkward size, could contribute to such problems as carpal tunnel syndrome of the wrist, which further defines ergonomic problems with respect to the disadvantages of such heavy fluid products as related to the U.S. Pat. No. 5,792,126 reference. U.S. Pat. No. 5,960,837 to Cude et. al., discloses a suction canister and lid combination whereby only destructive force will separate the parts. This renders this invention a disposable product which is costly whereby each time a canister is used, another purchase is made by the customer, and another product enters internal distribution increasing cost cycles and increasing inventory handling costs and another piece of garbage enters the waste stream which is a serious disadvantage. This makes the system expensive, and requires ongoing internal distribution, requiring ongoing inventory space, which is at a premium in most institutions. Another disadvantage is the lack of choice for the customer to re-process, re-sterilize, or re-use, of which options are beneficial, but not available with the U.S. Pat. No. 5,960,837 reference. U.S. Pat. No. 5,901,717 to Dunn et. al., discloses a canister and flushing system. This system comprises complex equipment for handling a collection canister. The disadvantages to this system are expensive equipment is required, and such complex equipment needs expensive maintenance plus required periodic inspection which increases labor costs associated with its presence. In addition, the equipment must be kept clean, which is additional labor required for daily operations. Other disadvantages include a re-usable canister which requires costly labor for internal processing, re-processing and re-using. In most institutions volume of such collection systems is quite high imposing expensive internal handling and re-use processing costs. The system discloses a disposable flush kit which maintains higher disposable costs along with higher costs associated with internal distribution and inventory handling. U.S. Pat. No. 4,419,093 to Deaton discloses a reusable canister having a disposable lid and liner. This system is delivered in pieces and require subassembly by the customer prior to operation. This requires additional labor, which is costly, and involves the inventory and tracking of a plurality of systems in sets. Often times lids and liners can become separated and when out of numerical matching balance, one cannot be used without the other whereas resulting in an incomplete set and an unusable sub-assembly. This disadvantage complicates the ongoing internal distribution and tracking of the subassembly components, which adds costly labor, inventory management and excess handling. The U.S. Pat. No. 4,419, 093 reference also discloses contribution of garbage to the waste stream with each use which is a serious environmental concern.

DESCRIPTION OF THE INVENTION

The present invention provides methods and apparatus for utilizing product transfer/delivery containers which do not embody the self inherent physical capacity to maintain shape under extreme negative vacuum pressures of up to minus one atmospheres. Examples of cost effectively fabricated containers which do not embody the implosion resistant strength/construction needed for suction/vacuum collection, may include plastic delivery containers such as plastic pour bottles and intravenous solution containers. The present invention discloses cost effective solutions for reducing waste, reducing labor, reducing inventory, reducing internal distribution and reducing inventory handling costs involved with the collection of waste materials. These achievements are carried out by the instant invention whereby successful suction/vacuum collection may be realized using flexible cost effectively fabricated product solution transfer/delivery containers. This application discloses a collection system that teaches use of product supply containers for removal of waste material and the disposal chain. In particular delivery containers for general distribution/transfer/supply/delivery of pour bottle solutions and intravenous solutions and the like are converted into the waste collection and disposal chain. This application also teaches use of a common container for both the supply and disposal chain. This application also teaches use of containers in inventory for supply/delivery then transforming them for disposal utility. This application teaches the use of a common container for the product transfer and then integrates them into systems for the collection of waste material. This application teaches waste reduction methods by integrating delivery container fabrication and the collecting and disposing of waste materials of waste material with a cycling technique. This application teaches the waste reduction methods by using manufacturing methods such as blow molding, and blow fill seal container fabrication, and intravenous solution container manufacturing methods for delivery and disposal purposes transforming the container, which is derived from a delivery mode, from product transfer, and converting to collection of waste materials. The invention(s) of the instant case provide container utility options for the transfer of products, consumption of products and for waste collection options. The invention of the instant case discloses the utilization of product transfer containers, such as pour bottles and intravenous solution containers (bags)(and/or other product containing enclosures used for IV therapeutics and administration of anesthetic agents as well as other agents) for the receiving, collecting and containment and disposal of waste. Using product distribution/transfer containers, also for the handling of waste, results in optimal reduction of waste, reduction of inventory, reduction in labor, reduction of internal inventory distribution, and reduction of inventory and waste disposal costs because the need for separate disposal containers is reduced. The question arises, why pay for a disposal container when a delivery container can be derived from the supply side and converted into a disposal container. Such containers are supplied clean and well suited, within the scope of the instant invention for conversion/transformation into disposal containers. The instant invention confers options allowing consumer choices for the reduction of waste. Plastic transfer containers are commonly used for the distribution/transfer of sterile liquids and other products, such as sterile water, sterile sodium chloride irrigation solution, intravenous solutions for IV therapeutics, other solutions, and the like. These solutions are used for intravenous therapeutics, administration of anesthesia, wound irrigation, irrigation for arthroscopic/endoscopic procedures, urology procedures and many other types of uses. The inventor of the instant case names additional fluent material delivered in polypropylene and or polyethylene polyvinyl chloride containers which are generally high volume supplies in and/or engage the supply chain on a just in time basis for delivery/consumption. Intravenous solution containers (IV bags) are also used for the distribution/ commercialization of container products. It is understood the disclosed teachings are not limited to sterile distribution/ commercialization product transfer containers. Other product transfer containers may be suitably integrated with the inventions concept to function in a disposal and waste reduction capacity. Other containers, such as prep solution containers, alcohol containers, solvents, and cleaning solutions may function suitably within the scope of the present invention. The teachings are not intended to limit the novel concept of waste reduction to any particular type of product distribution/commercialization transfer container. Other product containers may also be used in the instant invention. These "product" delivery containers are commercialized/ distributed to the customer having volumes sufficient enough to provide cubic capacity in substantial proportion for the collection and disposal waste materials. The instant invention(s) reduces the amount of plastic introduced into the waste stream. The instant invention reduces the re-cycling, reprocessing, and labor associated with handling and re-use procedures thereby lowering the associated costs of the waste collection/disposal processes. Collecting fluent waste materials in converted delivery containers such as a pour bottles and intravenous solution containers which have been cost effectively fabricated without implosion resistant strength/construction, provides various solutions/options solving the disadvantages/problems of such prior art containers when the methods and apparatus of the present invention are utilized. When the methods and apparatus embodied by the teachings of the present invention are utilized, the instant invention also provides solutions for reducing the handling and reducing labor, and reducing the costly processes of re-cycling, reusing, reprocessing, sterilizing and/or re-sterilizing. Certain product delivery/transfer containers are fabricated, commercialized and already present or in the supply/distribution chain and or in the consumer facility. The present invention conveniently and easily transforms, converts and integrates these transfer delivery containers for transformation into waste materials collection vessels creating a new type of environmental cycle. We refer to this new/novel cycle as a Techni-cycle. Therefore, Techni-cycling defines a new methods and apparatus of using technique to cycle containers from the delivery side of consumption to the disposal side of consumption for environmental purposes. In essence, Techni-cycling defines the novel process of converting a delivery container into a waste receptacle. In essence, Techni-cycling is also defined by deriving waste receptacles from incoming delivery supplies. In essence, Techni-cycling is defined by transforming delivery containers into disposal containers. In essence, Techni-cycling is an environmental conversion and transformation method. In essence Techni-cycling confers the options and advantages as disclosed in the instant application. In essence, Techni-cycling is the environmentally preferred method. In essence, Techni-cycling is environmental, among other things. Difficulties exist with the use of the certain pour bottles when integrated in a high negative pressure vacuum collection system. Difficulties also exist with the use of intravenous solution containers when integrated in a high negative vacuum system as commonly used in suction/vacuum collection of surgical waste materials. Negative vacuum draw pressure, at times up to −1 atmospheric pressure is common for drawing surgical waste materials from a surgical site into collection receptacles. One problem is that the common pour bottles are cost effectively manufactured with relatively thin plastic walls sometimes down to the range of 0.025 inches thick, or less and generally made with plasticized materials such as high density polyethylene, polypropylene, polyvinyl chloride, or other like materials. Thin walled containers are commonly fabricated to reduce the plastic material mass (volume of plastic material per unit) and hold down production costs, and shipping weight. It is common practice in container manufacturing to consume the minimum amount of material used per unit to fabricate each container yet maintain end user function for cost effective manufacturing purposes. Common container material durometers, comprising containers having such ranges of thin wall thickness in these like materials, are not generally strong enough to withstand the negative differential pressure of up to −1 atmosphere found in a suction vacuum system, without imploding and/or deforming. Product distribution/transfer containers are commonly fabricated using manufacturing processes know by artisans skilled in the arts of blow molding, and/or blow fill seal manufacturing and the process of thermally laminating sheets and forming cavities for the filling and the production of intravenous solution containers. These containers are fabricated open top or closed top. A solution to the problem of bottle deformity which occurs under high negative implosion pressure is to connect the pour bottle to a suction collection system whereby the pour bottle wall is interposed, between its inner chamber and an outer interspace, each space subjected to a common draw force, the force enveloped over itself on the container inside and outside, the which forms opposing differential pressures providing wall reinforcing balances by effecting a positive and negative neutral force on the bottle wall balancing negative implosion forces. This is carried out by the container and canister co-acting to contain and balance forces in the composite draw path. This addresses the issue of bottle deformity.

The instant invention discloses the neck of a pour bottle as a utilitarian area of the bottle for coupling with a canister system. The instant invention discloses a throat space aperture (pour spout) of a plastic pour bottle as a utilitarian area for engagement of a draw force. The instant invention discloses the throat space aperture (pour spout) as a utilitarian area for coupling of a throat aperture plug. The instant invention discloses a positive and negative pressure exchange plug for providing communication between the draw force and the inside and outside of a transfer container. The instant invention discloses locating an atmospheric pressure draw exchange at the neck area of a transfer container. The present invention discloses interposing the neck (pour spout) of a product transfer/delivery bottle for conversion circumferentially between an throat/aperture plug and a canister lid/cover. In an alternative embodiment a bottle neck cap is interposed between a bottle neck and a canister lid/cover. In still a further embodiment a downward projecting hollow boss is interposed circumferentially between a bottle neck and a force exchange plug. The present invention discloses fabricating a blow molded container for transformation/conversion and bayonet coupling to a canister system. It is understood that that the invention is not intended to be limited to bottle neck configurations which are round. Any shaped bottle neck/lid-cover, cap, plug, boss configuration suitable for arrangement/construction having structuration to carry out the utility of the present invention may be fabricated to carry out the purposes of the instant case. The present invention discloses positioning the plastic bottle throat space in a pressure draw system whereby an in-drawn force is disposed to transfer and deposit medical waste materials into the bottle and an out-drawn force is disposed to transfer the differential draw forces. The present invention utilizes the inner chamber of a plastic pour bottle as a part of the pressure draw communication system. The present invention discloses several embodiments for carrying out the invention. In one embodiment, a bottle cap is shown guiding the exchanging forces in a position along a force draw path at a location between a site of waste material (surgical site) and a source from which the draw forces emanate. The cap is connectable to a lid/cover which attaches to a canister body. In a second embodiment a bottle neck is circumferentially (not necessarily meaning round) interposed between a lid (second embodiment) and a throat spacer (pressure exchanger), whereby the throat spacer is disposed in guiding position to exchange forces along a draw path at a location between a site of waste material (surgical site/other source) and a source from which draw forces emanate. In another embodiment a downward directing hollow lid boss is fitted into a bottle throat and the lid boss is circumferentially (not necessarily meaning round) interposed between a bottle neck and a hollow lid boss transfer plug. The lid aperture spacer is disposed to guide and exchange differential draw forces along a force draw path at a location between a site of material waste (surgical site) and a source from which the draw forces emanate. In another embodiment a plastic pour bottle comprises a neck area comprising winged locking lugs formed unitary with the bottle and disposed to connect to a canister lid embodiment by bayonet motion. Throat/aperture spacers may then be placed in the throat space of the plastic bottle in a position to guide exchange forces along a draw path at a location between a source of waste material (surgical site/other source) and a source from which the draw force emanates. The inventor/author knows of no prior art which anticipates the proximate function and/or provides the utility of the present invention disclosed in this patent application.

PURPOSE OF THE INVENTION

One object of the invention is to fabricate a delivery container for disposal and coupling to a waste collection system. Another objective of the invention is to provide a delivery and collection container system using bottles fabricated from a blow molding process. Another object of the invention is to provide a delivery and collection container fabricated from a blow fill seal manufacturing process. Another object of the invention is to provide a suction/vacuum system which renders product distribution/transfer containers receptive to waste materials. Another object of the invention is to provide a collection system for reducing waste that is derived from a product delivery. Still a further purpose of the invention is to provide container options for reducing the amount of material waste introduced to the waste stream in the medical field. Another object of the invention is to deposit waste materials into a container derived from the product transfer distribution/commercialization cycle and converted into a waste receptacle. Another object of the invention is to use intravenous solution containers as converted receptacles for waste materials. Another object of the invention is to use pour bottles and convert them as receptacles for waste materials. Another object of the invention is to fabricate a waste reducing system which conveys waste reduction options. Another purpose of the invention is to reduce the internal distribution, the inventory management of surgical waste collection devices. Another purpose of the invention is to provide methods and apparatus effecting the utility of reducing handling associated with the collection of surgical material waste. A further purpose of the invention is to provide methods and apparatus to reduce re-cycling, re-processing, and re-use procedures. Still a further object of the invention is to fabricate systems which utilize the cubic space capacity embodied in product distribution, delivery and transfer containers such as pour bottles and intravenous solution containers for waste collection and disposal. Yet another object of the invention is to provide methods and apparatus for the consumer to account for cubic volumes of incoming fluids and cubic volumes of outgoing waste materials for cost effectiveness and better supply planning and purchasing. And still a further object of the invention is to provide methods and apparatus in a system that provides cost effective container conversion and transformation procedure, supply planning, ordering, inventory carrying, procedure supply selection and supply utility. Yet another object of the invention is to provide more cost effective means for collecting surgical waste materials. Still a further object of the invention is to interpose the inner chamber of a plastic pour bottle along an draw path at a location between a material waste source (surgical site) and a source from which the draw force emanates. Still a further object of the invention is to provide a suction collection system fabricated to connect to a pour bottle. Still a further object of the invention is to provide a suction/vacuum system to connect to an intravenous solution container. Still a further object of the invention is to fabricate a blow molded bottle to fit to a suction canister system by a bayonet movement. Still a further object of the invention is to provide a blow molded container comprising a neck structuration for coupling to a lid/cover boss. Still a further object of the invention is to integrate the inside of a distribution/commercialization product transfer container into the vacuum/suction draw control path for reception of waste materials. Still a further object of the invention is to reinforce the walls of a product distribution/commercialization using a vacuum/suction force. Still a further object of the invention is to interpose a transfer container along an intermediate portion of a draw control path between a vacuum/suction source and a source of waste material. Still a further object of the invention is deposit waste materials into a product distribution/commercialization transfer container by a draw force. Still a further object of the invention is to couple a canister cover to a product distribution/transfer container. Still a further object of the invention is to fabricate a product transfer container to couple to a canister cover. Still a further object of the invention is to fabricate a container and a canister cover to couple together. Yet another object of the invention is to provide for container Technicycling (as defined above)

BRIEF DESCRIPTION OF THE DRAWINGS

FIG. 1 is a top perspective view of a plastic pour bottle disposed in a surgical suction/vacuum canister system for receiving material waste deposits.

FIG. 2 is a partial top perspective of a pour bottle coupled to a bottle cap and connected to canister lid embodiment 1.

FIG. 3 is a top perspective view of a plastic pour bottle disposed within a surgical suction/vacuum canister system that has a side vacuum draw port.

FIG. 4 is a top perspective view of a plastic pour bottle disposed within a surgical suction/vacuum canister system as a receptacle for the collection of surgical material waste deposits and the suction canister housing body has a side vacuum/suction draw port.

FIG. 17a is a partial cross section view of surgical canister lid embodiment 2 coupled to the outer contour of a plastic pour bottle neck having the bottle disposed therewith to receive throat aperture force exchange plug 7 of FIG. 17. The plastic pour bottle annularly interposable along its neck portion between throat/aperture force transfer plug 7 and surgical suction canister lid embodiment 2 and disposed as a receptacle to receive waste material.

FIG. 23 is a cross section view of throat aperture vacuum transfer plug 7c shown with an outdraw filter 35 and separate and releasably coupable with suction tubing in-draw spike 9 through 9a.

FIG. 25 shows a side elevation of a suction tip connected to a suction tubing.

FIG. 26 is a side elevation view of the throat/aperture plug vacuum transfer plug 7b of FIG. 22.

FIG. 27 is a cross sectional view of the throat/aperture vacuum transfer plug of FIG. 23.

FIG. 28 is a side elevational view of throat/aperture plug 7d having a outline filter releasably coupled to the plug and having a suction tubing releasably coupled to material in-draw spike 9 through 9a. Each of FIGS. 26, 27, and 28 shows throat/aperture plugs connectable to a suction tubing and the suction tubing as shown in side elevational view FIG. 25 as connected to a suction tip 19.

FIG. 29 is a partial exploded cross sectional view of a surgical suction canister lid embodiment 3 1b having an aperture annularly surrounded by downward boss disposed to fit in the throat of a pour bottle.

FIG. 30 shows a pour bottle embodiment 2, 4c having a O-ring seal platform/flange located on the neck of the pour bottle and integrated in a unitary fashion and a pair of locking lug wings.

FIG. 31 shows a partial exploded cross sectional and side elevation view of pour bottle embodiment 2, 4c of FIG. 30 in perspective alignment with a partial side elevational view of surgical suction canister lid embodiment 1. Plastic pour bottle 4c is shown to assemble with lid embodiment 1 for connection to any number of canisters housings sizes.

FIGS. 32, 33, 34, & 35 show various throat/aperture vacuum transfer plug embodiments each connectable as shown by the four connection lines 32 and each shown by lines 33 to be placed down the throat of suction pour bottle 2 4c, the partial side elevational view of suction canister lid embodiment 1 shown connectable to plastic pour bottle embodiment 2 and interposable between a pour bottle and a throat/aperture vacuum transfer plug.

FIG. 36 shows a side elevation of a suction tip 19 and suction tubing 16.

DETAILED DESCRIPTION OF THE DRAWINGS

Figure 5:
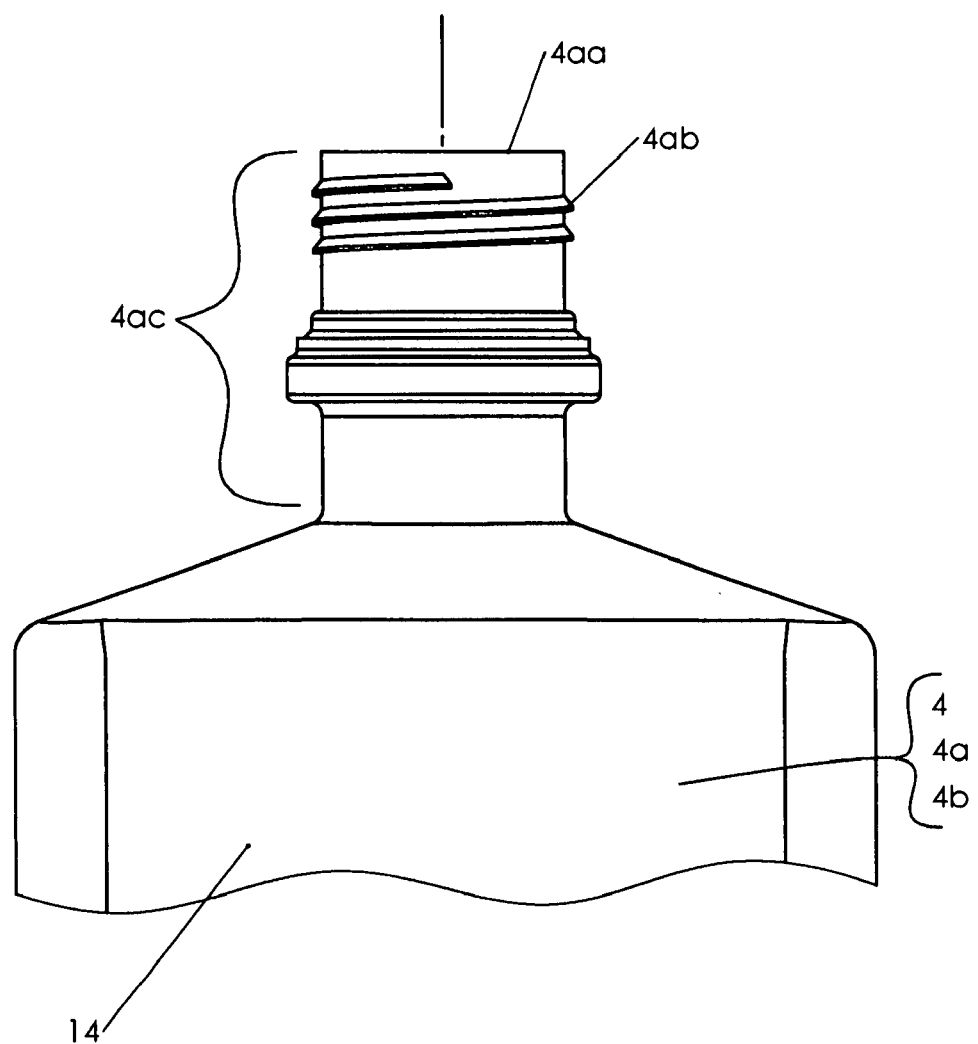
FIG. 5 is a partial side elevational view of a plastic pour bottle and neck.

Turning to FIG. 1. FIG. 1 shows a plastic pour bottle 4 disposed within a surgical suction/vacuum collection system. The collection system comprises canister body 3, canister cover lid 1, pressure differential thru-put cap 2, plastic pour bottle 4, integrally connected to form a surgical suction/vacuum collection system. Differential vacuum draw pressure emanates from an external source 18 and is controlled through vacuum tubing 12 which is connected to lid 1 at tubing port 13. Interspace 5 is a vacuum balance space which is interposed between the exterior of plastic bottle 4 and the interior of the lid 1 housing body 3 and cap 2 assembly. A negative atmospheric vacuum emanates at an external source 18 and is drawn through tubing 12 and induces a negative vacuum draw in interspace 5 by connection to tubing port 13. The negative atmospheric vacuum draw communicates with the inside chamber 14 of pour bottle 4 by means of tubing 6 which is connected at one end to lid 1 at tubing port 15 and at the other end at elbow connector 17. Elbow 17 is connected to tubing 6 at one end and connected to cap 2 at the other end. Tubing 6 connects interspace 5 to the interior chamber 14 of plastic bottle 4 transferring the negative atmospheric pressure draw vacuum to in-draw suction tubing 16 which is connected to cap 2 at in-draw port 8.

Turning to FIG. 2. FIG. 2 shows pour bottle 4 connected to cap 2 which in turn in connected to lid 1. Negative atmospheric pressure draw transfer conduits 6, 12 and 16 have been removed from lid ports 13 and 15 and cap ports 10 & 8. Lid 1 comprises wing passage space 1aa shown in two locations for the thru-put of cap wings 2a shown in two locations. Lower wing surface 2d is shown having made contact with lid ramp surface 1ab. Pour bottle 4 is shown connected to cap 2, and cap 2 is shown with its wings 2a having been inserted through lid slots 1aa and rotated such that lower wing surfaces 2d contact lid ramps 1ab causing an increased contact tension-pressure seal between cap 2 and lid 1.

Turning to FIG. 3. FIG. 3 shows a round plastic pour bottle 4a inserted into a surgical suction collection system. This figure depicts a surgical suction collection system having a similar differential vacuum draw pressure system to that of FIG. 1 however the housing canister housing body of the system of FIG. 3 embodies a side mounted vacuum port structure 13a as shown being connected to a suction tubing 12a which in turn is disposed to transfer a negative atmospheric differential pressure draw emanating from an external source 18.

Turning to FIG. 4. FIG. 4 shows a rectangular shaped plastic pour bottle 4b connected to a surgical vacuum suction collection system. The surgical suction vacuum collection system of FIG. 4 has similar negative atmospheric differential draw pressure features as the embodiments of FIG. 1 and FIG. 3. FIG. 4 shows the plastic pour bottle 4b as having a rectangular shaped body and similar to FIG. 3 shows canister housing body 3a embodied with a side port vacuum draw 13a which is in turn connectable to a suction tubing 12a which in turn leads to an external negative differential pressure draw source 18.

Turning to FIG. 5. FIG. 5 shows features of a plastic pour bottle 4, 4a & 4b depicting a square, round and/or rectangular pour bottle body shapes. Plastic pour bottle 4 has an interior chamber 14, a pour spout/throat/aperture descending the interior neck forming into the plastic pour bottle chamber 14, a neck portion 4ac and the neck portion 4ac having an external threaded portion 4ab.

Figure 6:
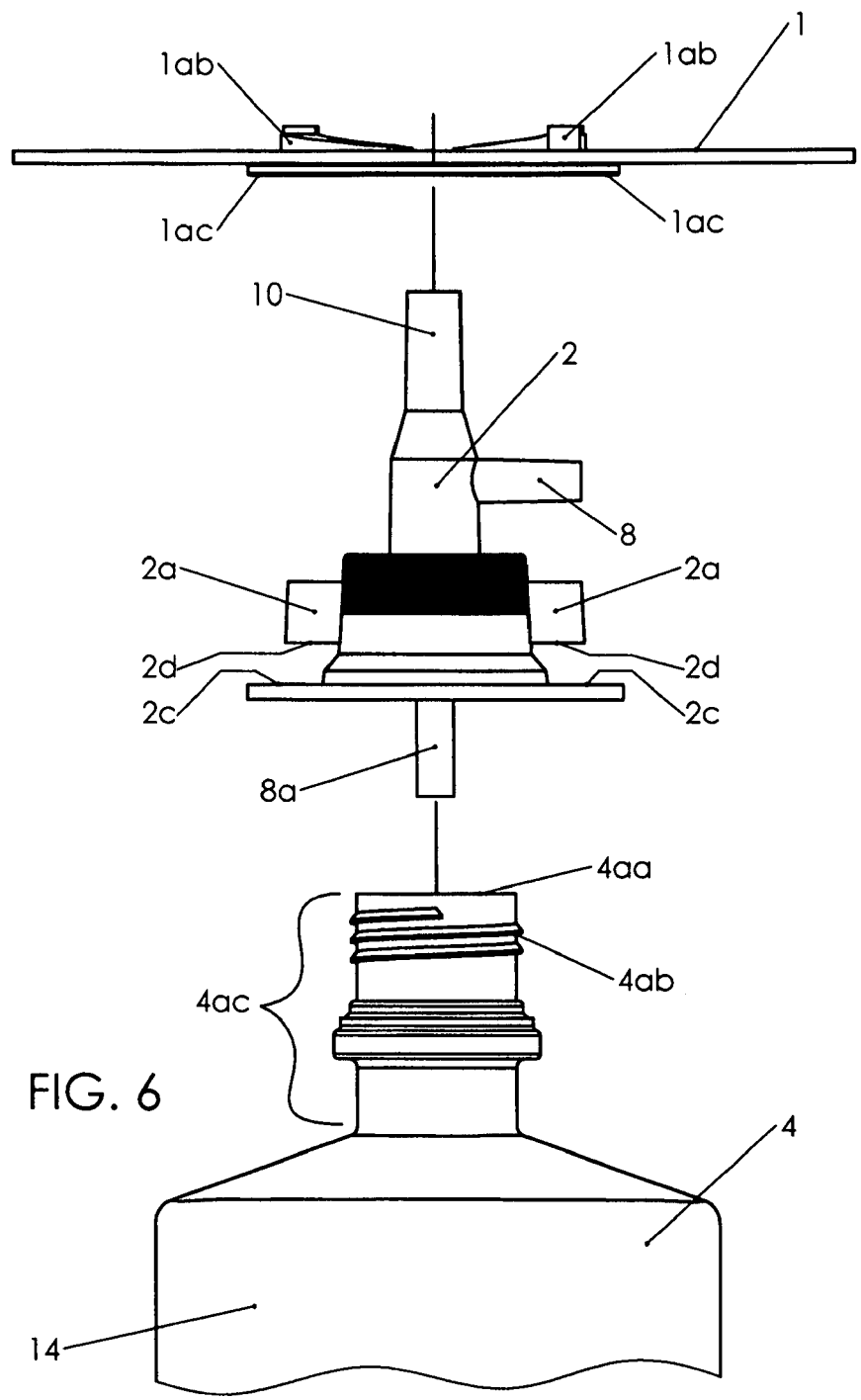
FIG. 6 is an exploded side elevational view of a plastic pour bottle, a bottle vacuum pressure exchange cap and a partial side elevation view of lid embodiment 1.

Turning to FIG. 6. FIG. 6 shows plastic pour bottle 4, bottle cap 2, and lid embodiment 1 in a exploded view showing the relationship of the connectability of these three pieces. Plastic pour bottle neck 4ac is engages the lower portion of cap 2 engaging threads 4ab and bottle throat/aperture 4aa which is intended to contact the insides of cap 2. Cap 2 is shown with in-draw port 8 which communicates though in draw port 8a and disposed to deposit collection materials into the inside chamber 14 of pour plastic pour bottle 4. Bottle cap flange 2c extends circumferentially outward with an upper surface intended to mate with an O-ring disposed in an O-ring groove 1ac. (not shown) Wings 2a are sized to pass through slots 1aa shown in FIG. 2. Lower surface wing 2d is intended to rotatably engage lid ramps 1ab of FIG. 2 through twisting engagement to accomplish increasing contact seal between cap 2 at 2c and O-ring 21 as shown in FIG. 7, FIG. 8 and FIG. 9.

Figure 7:
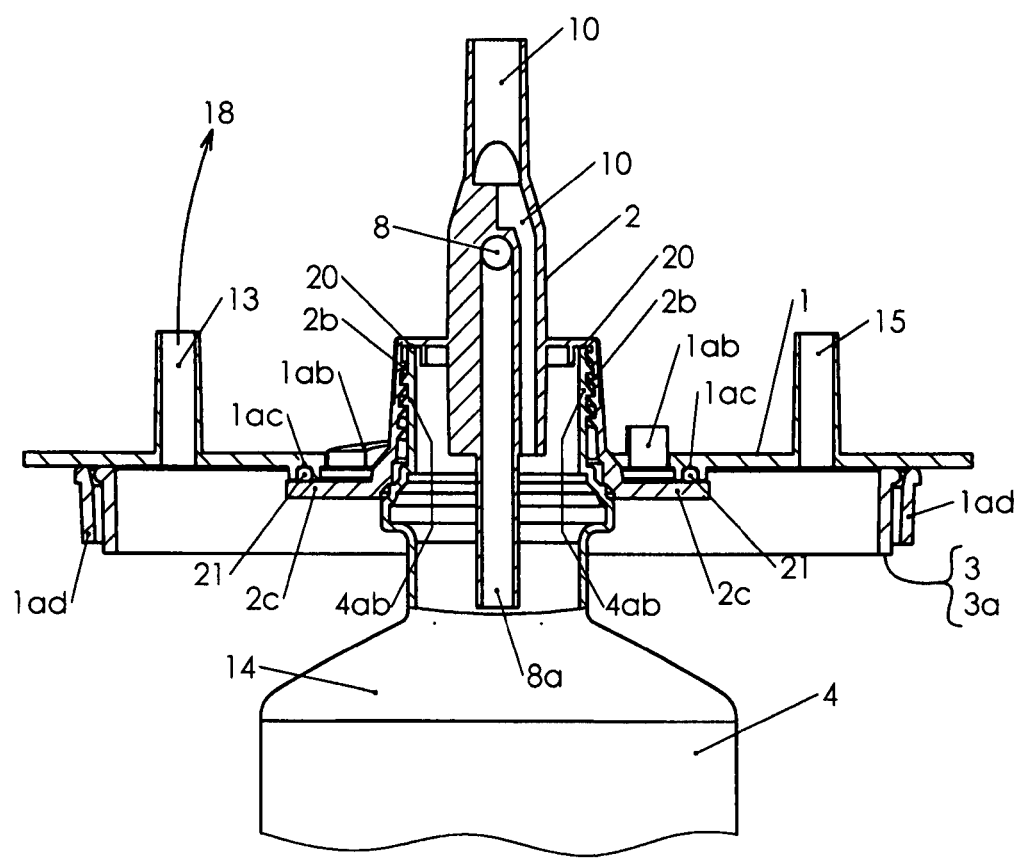
FIG. 7 is a partial cross section view of a plastic pour bottle disposed as a receptacle for receiving deposits of surgical material waste connected to a vacuum transfer cap which is in turn connected to canister lid embodiment 1.

Turning to FIG. 7. FIG. 7 is a partial cross sectional view of a plastic pour bottle 4 having its upper neck section connected to cap 2 which in turn is connected to lid embodiment 1 which is in turn connected to the top of canister body housing 3 at 3a. Collection material in draw port 8 of cap 2 is shown communicating through material deposit port 8a which is disposed to deposit surgical suction collection material into inner chamber 14 of plastic pour bottle 4. Force control connections 13 and 15 of lid 1, connection 8 of cap 2 and connection 10 of cap 2 are shown with tubing connections removed. Lid embodiment 1 is shown with O-ring groove 1ac and O-ring 21. Cap 2 is shown with draw passage 10 which is in open communication through a split passage into the interior chamber 14 of plastic pour bottle 4. Plastic pour bottle 4 is shown as having threads 4ab which are in threaded engagement to cap threads 2b with sufficient contact to seal plastic pour bottle 4 rim into cap 2 at 2d. Lid embodiment 1 shows cap ring ramps 1ab with lug wings 2a (not shown) having sufficiently been rotated in contact with sealing ramp 1ab such that the peripheral cap flare 2c sufficiently forms a seal contact with O-ring 21.

Figure 8:
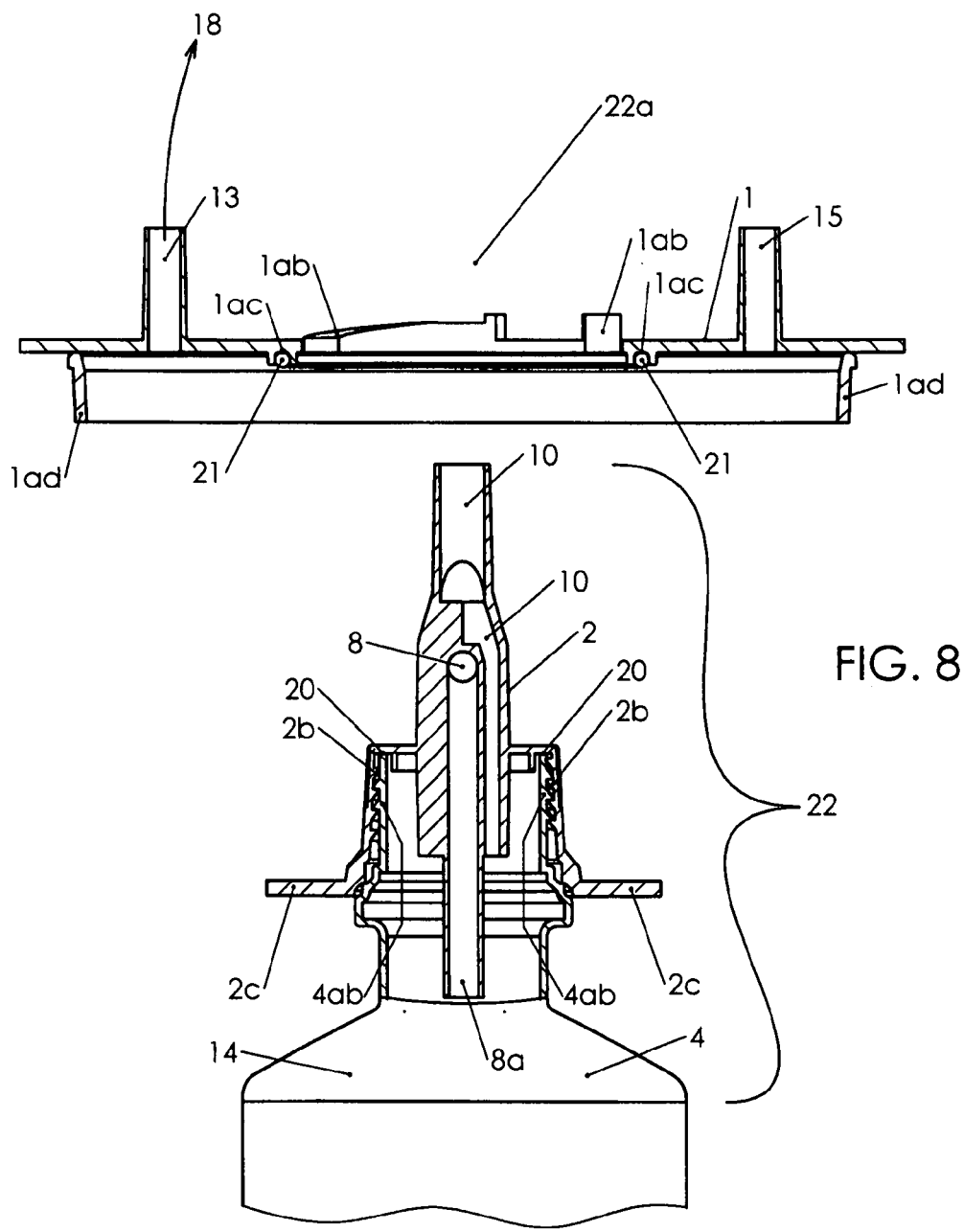
FIG. 8 is a partial exploded cross sectional side elevation depicting a plastic pour bottle connected to a vacuum transfer bottle cap pre-connected for subsequent connection to a lid embodiment 1.

Turning to FIG. 8. FIG. 8 shows plastic pour bottle 4 in a configuration connected to cap 2, defining a pre-assembly of plastic pour bottle 4 and cap 2, which may then be connected to a lid embodiment 1 in a fashion as described in FIG. 7. FIG. 8 shows a method of achieving a subassembly of FIG. 7 using a practice method whereby plastic pour bottle 4 and bottle cap 2 are pre-assembled for subsequent connection to lid embodiment 1 at a time determined most convenient by the user for purposes in the preparation of collecting surgical material waste.

Figure 9:
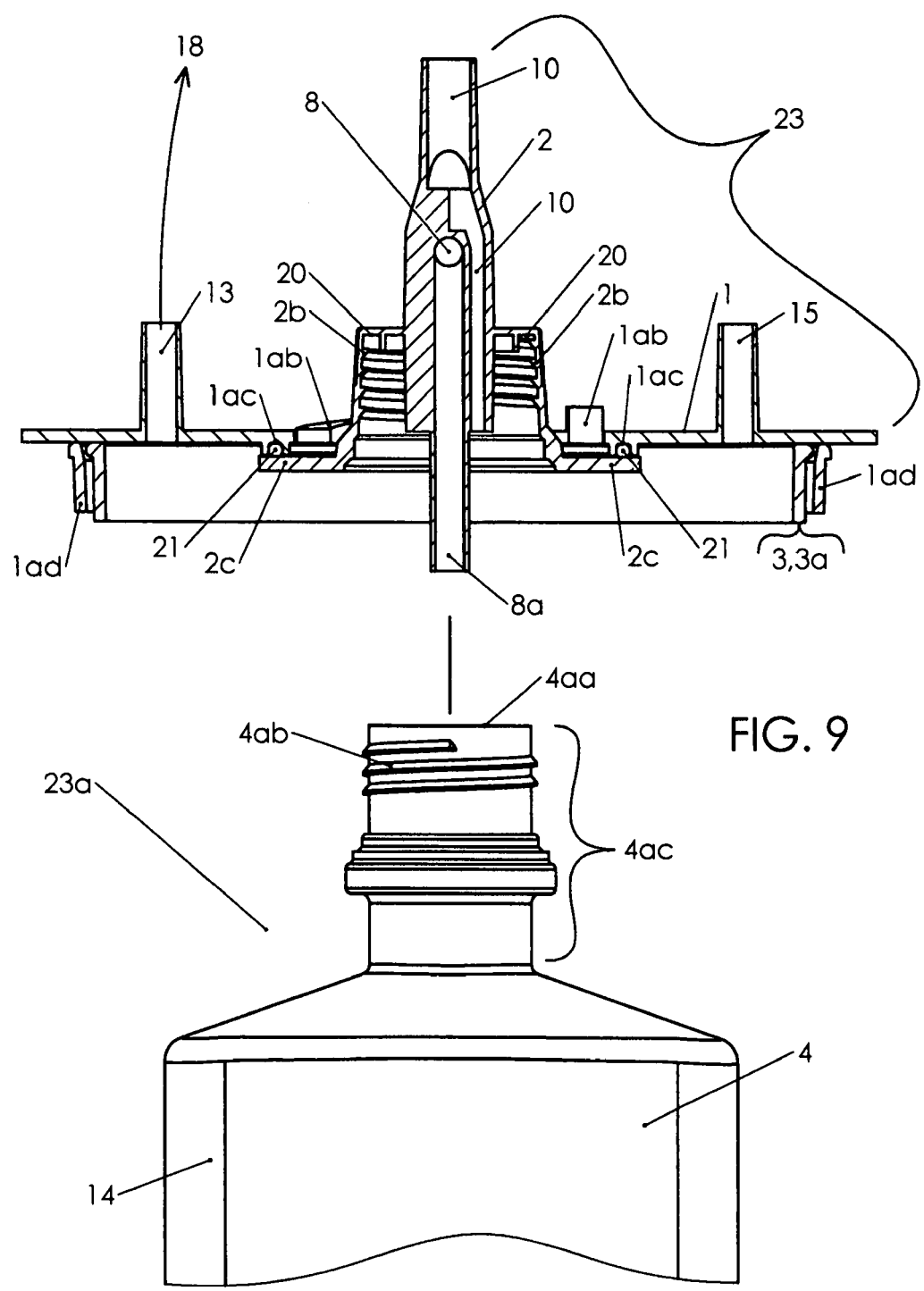
FIG. 9 is a partial exploded cross sectional/side elevational view of a bottle vacuum pressure transfer cap connected to canister lid embodiment 1 and a plastic pour bottle connectable to the cap and lid assembly for being disposed within a surgical suction/vacuum draw canister system as a receptacle for receiving surgical suction waste material deposits.

Turning to FIG. 9. FIG. 9 shows lid embodiment 1 sufficiently connected to bottle cap 2 as shown in FIG. 7. FIG. 9 depicts the pre-assembly of lid embodiment 1 and cap 2 which then in turn may be subsequently connected to plastic pour bottle 4 at a time determined most convenient in preparation of depositing surgical suction material waste in a plastic pour bottle.

Figure 10:
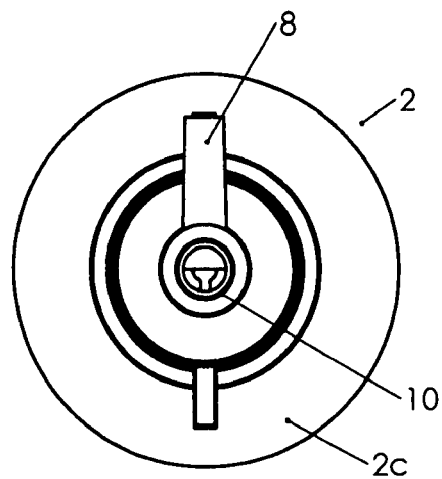
FIG. 10 is a top plan view of a plastic bottle vacuum transfer force exchange cap.

Turning to FIG. 10. FIG. 10 shows a trop view of bottle cap 2 showing vacuum material in-draw port 8 and outdraw vacuum port 10. Peripheral cap flange 2c is also shown.

Figure 10A:
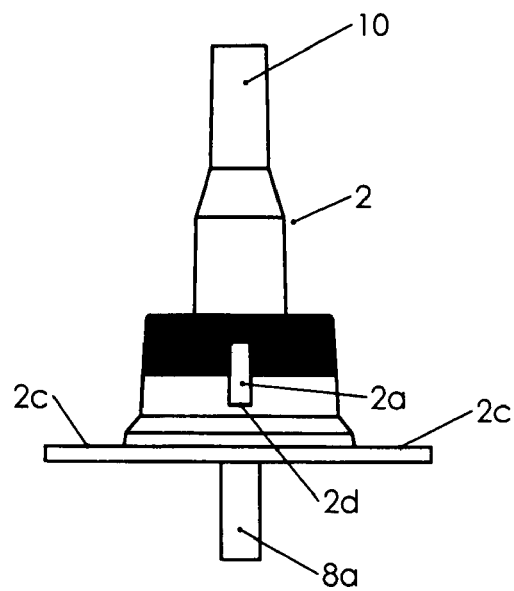
FIG. 10*a* is a side elevation view of the plastic bottle vacuum transfer cap.
Figure 10B:
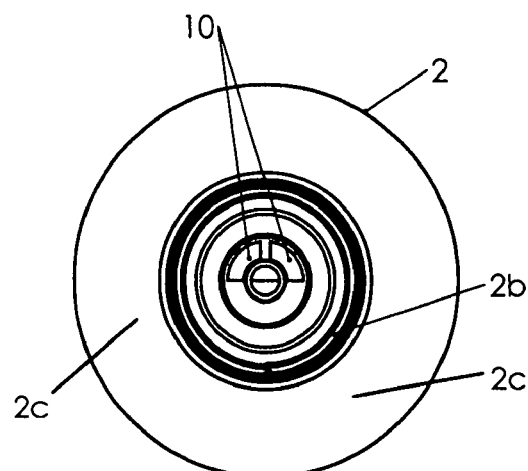
FIG. 10*b* is a bottom plan view of a plastic bottle vacuum transfer cap.

Turning to FIG. 10a. FIG. 10a shows a side elevation of bottle cap 2 showing outdraw vacuum port 10, lug wing 2a, lower wing contact surface 2d and cap seal contact surface 2c. Also shown is material deposit port 8a disposed to deposit waste material into chamber 14.

Figure 11:
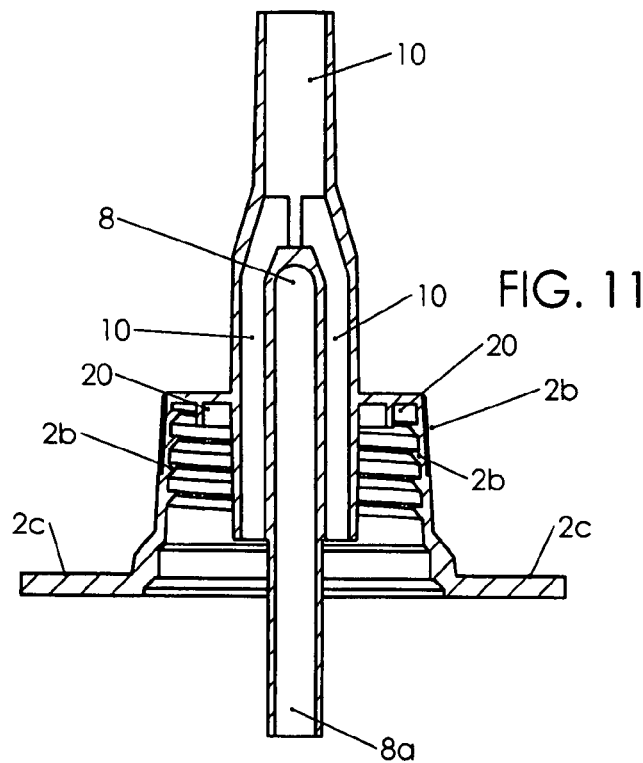
FIG. 11 is a cross sectional view with a perspective looking directly into in-draw port 8.

Turning to FIG. 11. FIG. 11 shows a cross section of cap 2 showing in-draw port 8 which communicates with chamber 14 through cap 2 into material deposit spout 8a. Outdraw port 10 is disposed to communicate with chamber 14 of a plastic pour bottle 4 through split passages 10. Pour bottle 4 rim engages with cap thread 2b and bottoms out with cap 2 at bottom 2d. Cap seal flat 2c is also shown.

Figure 11A:
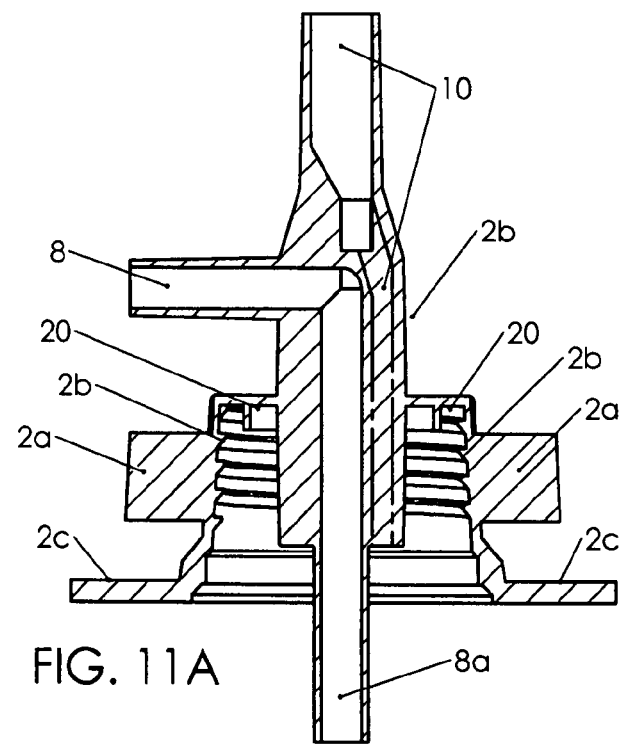
FIG. 11*a* is a cross sectional view with a perspective 90 degrees to that of FIG. 11 looking at a side perspective section of in-draw port 8 through 8*a*.

Turning to FIG. 11a. FIG. 11a shows a cross section cut 90 degrees to that of FIG. 11 showing material in-draw port 8 as it communicates with/through material deposit spout 8a. Cap 2 is shown with material draw passages 10 (dashed lines) and rotation wings 2a.

Figure 12:
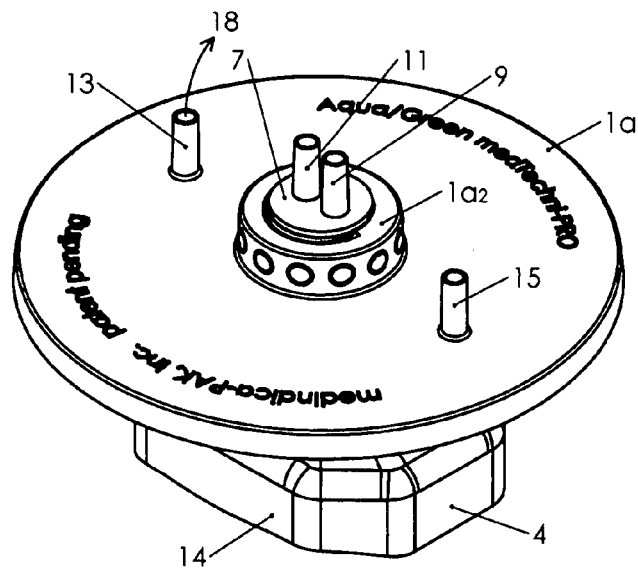
FIG. 12 is a partial top perspective of a plastic pour bottle connected to a surgical suction canister lid embodiment 2 and throat/aperture vacuum exchange plug 7.

Turning to FIG. 12. FIG. 12 shows a plastic pour bottle 4 having an interior chamber 14 connected to a suction canister housing lid embodiment 1a. Pour bottle 4 is shown with differential pressure draw thru-put throat/aperture plug 7. Tubing port 13 is disposed for connection with a source from which a vacuum draw force emanates, controlled by a vacuum draw tubing, and tubing port 15 is disposed for a connection to a tubing which in turn will be connected to out-draw vacuum port 9. Throat/aperture plug 7 is shown disposed with a material in-draw deposit port 11. Canister housing lid embodiment 2 1a is shown with a upwardly extending plastic bottle attachment boss 1a2.

Figure 13:
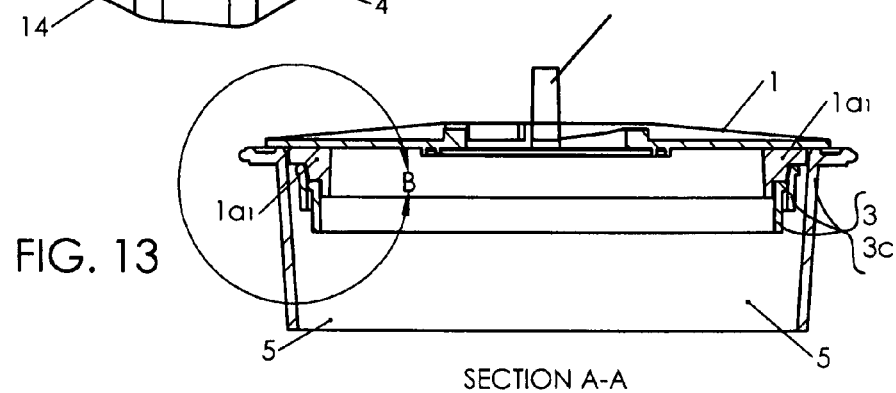
FIG. 13 is a partial cross section of a surgical suction canister lid 1*a*1 showing connectability to several sizes of surgical suction canisters by means of a multi-step ring bottom configuration.

Turning to FIG. 13. FIG. 13 shows a cross section of lid embodiment 1 comprising a multi-step base attachment 1a1 disposed for seal-able engagement with multiple sized/diameter canister housing bodies 3, 3a and 3b. FIG. 13 shows interposed space 5.

Figure 14:
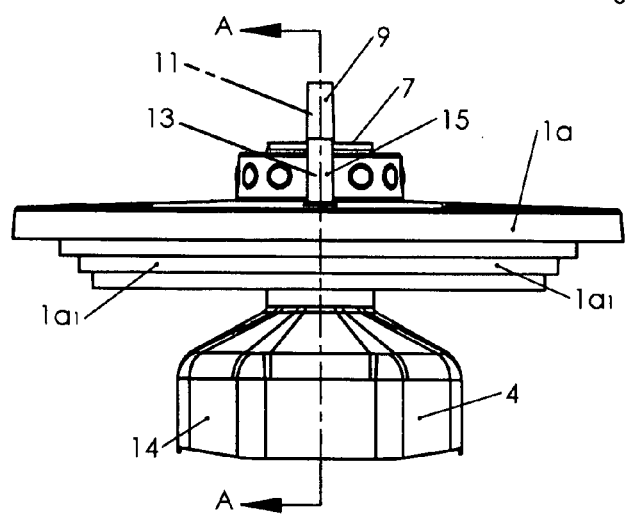
FIG. 14 is a partial side elevation of a surgical suction canister lid embodiment 2 connected to a plastic pour bottle disposed therewith as a receptacle for collecting surgical suction material waste deposits through throat/aperture vacuum exchange plug 7.

Turning to FIG. 14. FIG. 14 shows $2^{nd}$ lid embodiment 1a comprising unitary multi-canister fitting base 1a1, bottle connection boss 1a2 connected to plastic pour bottle 4, throat/aperture plug spacer 7, disposed to deposit material waste into the inside chamber 14 of plastic pour bottle 4. Tubing connector port 15 is shown. Tubing connector port 13 is not shown. Throat/aperture plug 7 is shown with material in-draw port structure 9. Material out-draw structure 11 is not shown.

Figure 15:
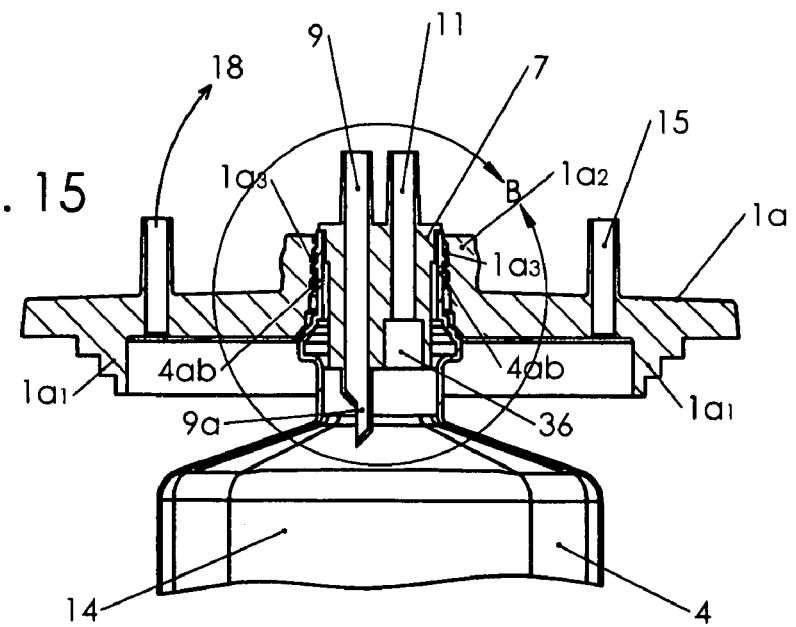
FIG. 15 is a partial cross sectional view of a portion of a plastic pour bottle neck interposed between a throat/aperture plug and a surgical suction canister lid embodiment 2 and disposed therewith as a receptacle for surgical suction waste material via means of throat/aperture plug 7.

Turning to FIG. 15. FIG. 15 is a partial cross section of $2^{nd}$ lid embodiment 1a as shown assembled with plastic pour bottle 4 and throat/aperture plug 7. Throat/aperture plug 7 is placed into the throat of pour bottle 4 for the purposes of positioning material in-draw deposit spout 9a such that materials drawn in through in-draw connector 9 deposit material into the inside chamber 14 of plastic pour bottle 4. Throat/aperture plug 7 shows tubing connection 11 and lid embodiment 1a and tubing connector 15. It is understood that as shown in FIG. 1, FIG. 3, FIG. 4 a tubing connection 6 is suitable for connecting connector 11 of throat/aperture spacer 7 with connector 15 of lid embodiment 2 1a. Plastic pour bottle 4 is shown with external neck thread 4ab as having been threadably engaged with lid embodiment 1a of lid boss 1a2.

Figure 16:
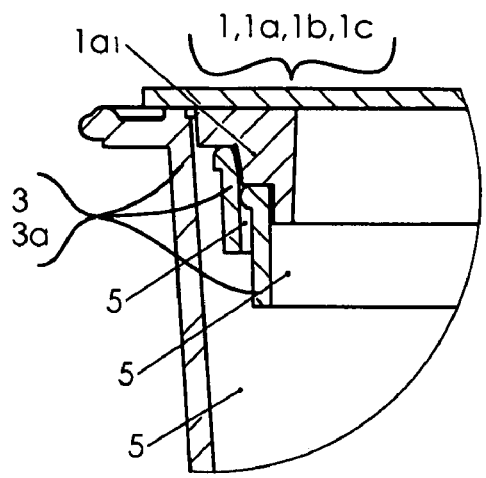
FIG. 16 is a partial cross section of surgical suction canister lid base 1a1 for adaptability to several sizes of suction canister body/housings.

Turning to FIG. 16. FIG. 16 is a partial cross section blow up of lid embodiments 1, 1a, 1b & 1c, each being depicted with multi-step base 1a1. Multi-step base 1a1 attaches to or is integrally/unitary with lid embodiments and is arranged to form a sealable coupling with various sizes of canister housing bodies 3 & 3*a*.

Figure 17:
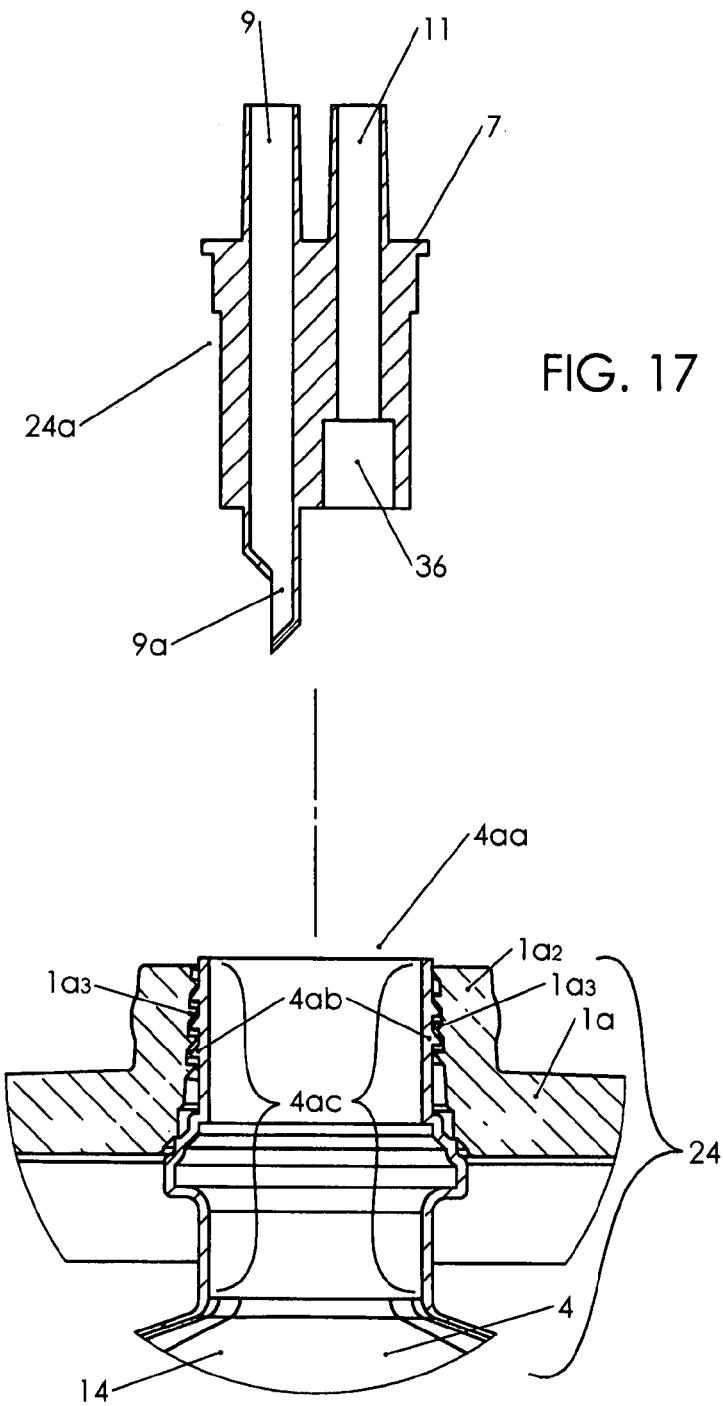
FIG. 17 is a cross section view of throat/aperture force exchange plug 7.

Turning to FIG. 17. FIG. 17 is a cross section of throat/aperture plug 7 having a throat in-draw connector 9 and vacuum out draw connector 11 with filter space 36 and material deposit spout 9*a*.

Turning to FIG. 17*a*. FIG. 17*a* shows pour bottle 4 external neck thread 4*ab*, threadably engaged to lid thread 1*a*3 of lid embodiment 1*a*. FIG. 17*a* shows how a pour bottle 4 and a canister lid 1*a* may be pre-assembled at a time or in a sequence which is determined to be convenient for the user in preparation of insertion of throat/aperture plug 7 for purposes in preparation of the depositing of suction collection material waste into chamber 14 of our bottle 4.

Figure 18:
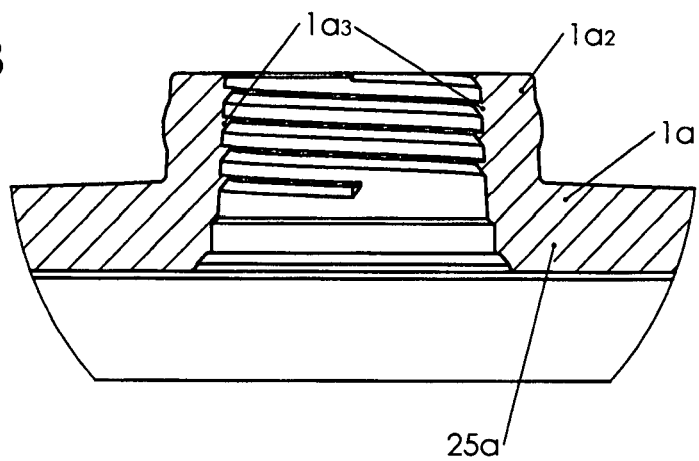
FIG. 18 is a partial cross sectional view of surgical suction canister lid embodiment 2.

Turning to FIG. 18. FIG. 18 is a partial cross section of lid embodiment 1*a* showing bottle engagement lid boss 1*a*2 and internal thread 1*a*3.

Figure 18A:
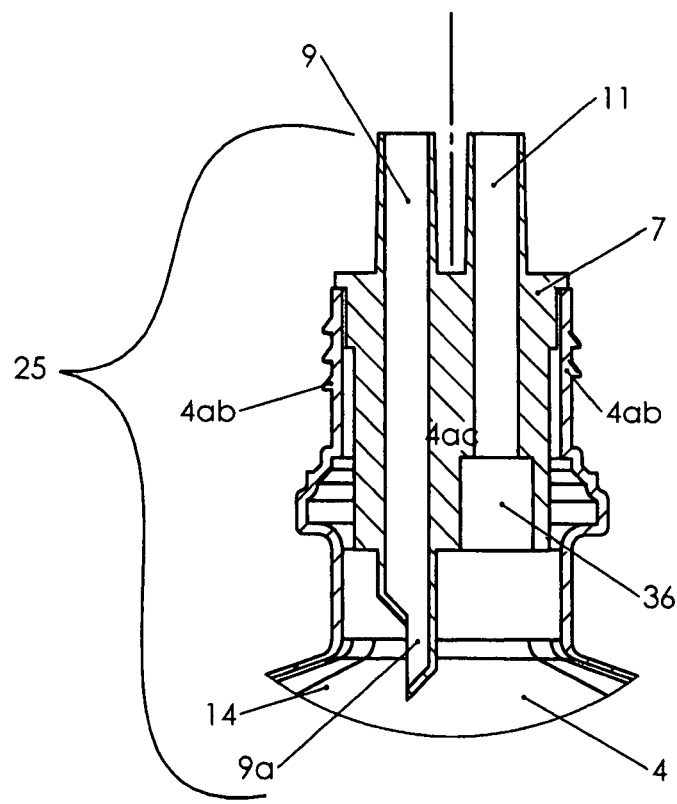
FIG. 18a is a partial cross sectional view of plastic pour bottle connected to throat/aperture vacuum transfer plug 7. The embodiment of FIG. 18a is shown connectable to the embodiment of FIG. 18.

Turning to FIG. 18*a*. FIG. 18*a* is a cross sectional sub-assembly of throat/aperture plug 7 inserted in the throat of pour bottle 4. FIG. 18*a* shows how throat/aperture 7 may be pre-connected to pour bottle 4 at a time or in a sequence which is determined to be convenient by the user in preparation for connection to lid embodiment 1*a* for the purposes in preparation of depositing surgical material waste into chamber 14 of pour bottle 4 through in-draw deposit spout 9*a*.

Figure 19:
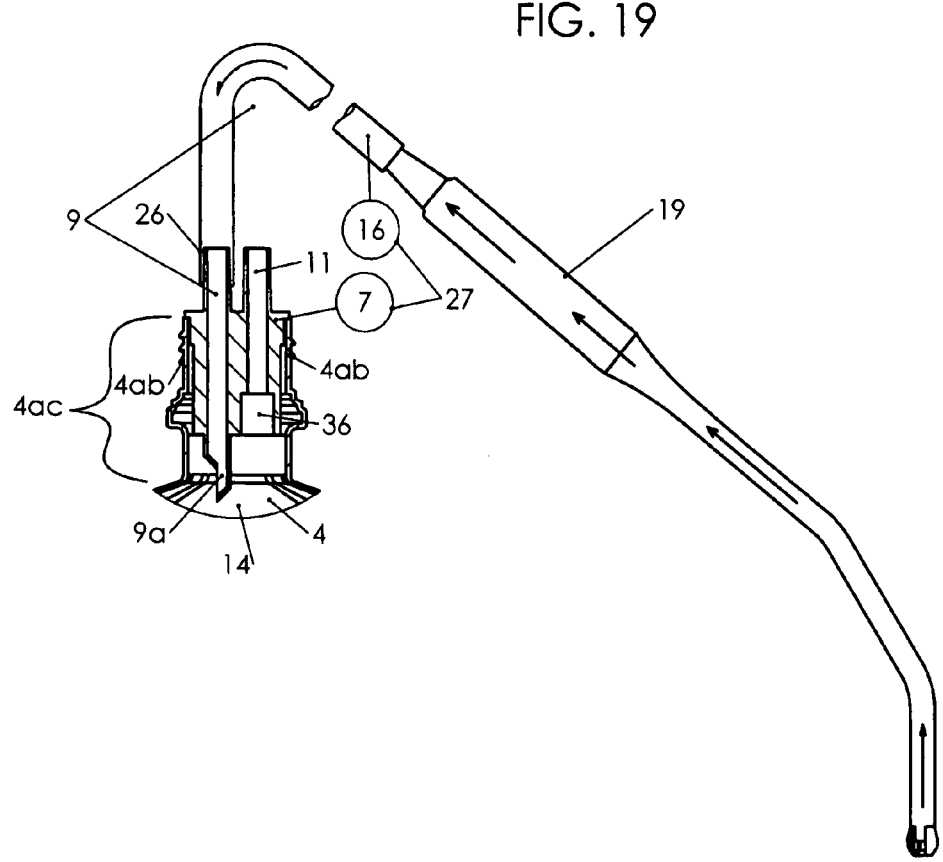
FIG. 19 is a partial cross sectional view of aplastic pour bottle connected to a throat/aperture vacuum transfer plug 7 which in turn is connected by an in-draw vacuum suction tubing and suction tip as shown in the side elevation view.

Turning to FIG. 19. FIG. 19 shows a cross section of embodiment of FIG. 18*a* with suction tubing 16 connected to in-draw port 9 at 26. Suction tubing 16 is shown connected to suction tip 19. It is understood that material in-draw line may comprise composite connections drawing material there-through and into the inner chamber 14 of pour bottle 4. It is also understood that drawing material waste into the inner chamber of a pour bottle may be carried out with a unified unitary material in-draw line. It is understood that this FIG. 19 may mean the in-draw line may comprise both a composite draw line or a unitary line.

Figure 20:
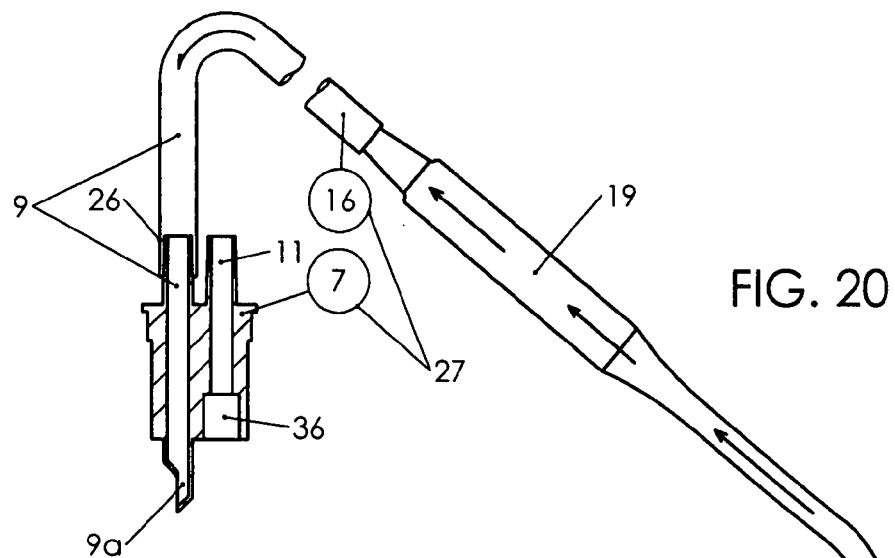
FIG. 20 is a cross section view of a throat/aperture vacuum transfer plug 7 as may be integrally and permanently connected to vacuum suction tubing pre-packaged, separately, with, or pre-connected to suction tip 19 as shown in the side elevation view.

Turning to FIG. 20. FIG. 20 is a cross section of the embodiment of FIG. 19 without the attachment of pour bottle 4. FIG. 20 depicts an embodiment wherein the in-draw line comprises composite connections between suction tip 19 and suction tubing 16 which is connected to in-draw port 9 at 26. Junction 26 may be permanently joined or may be releasably connectable.

Figure 21:
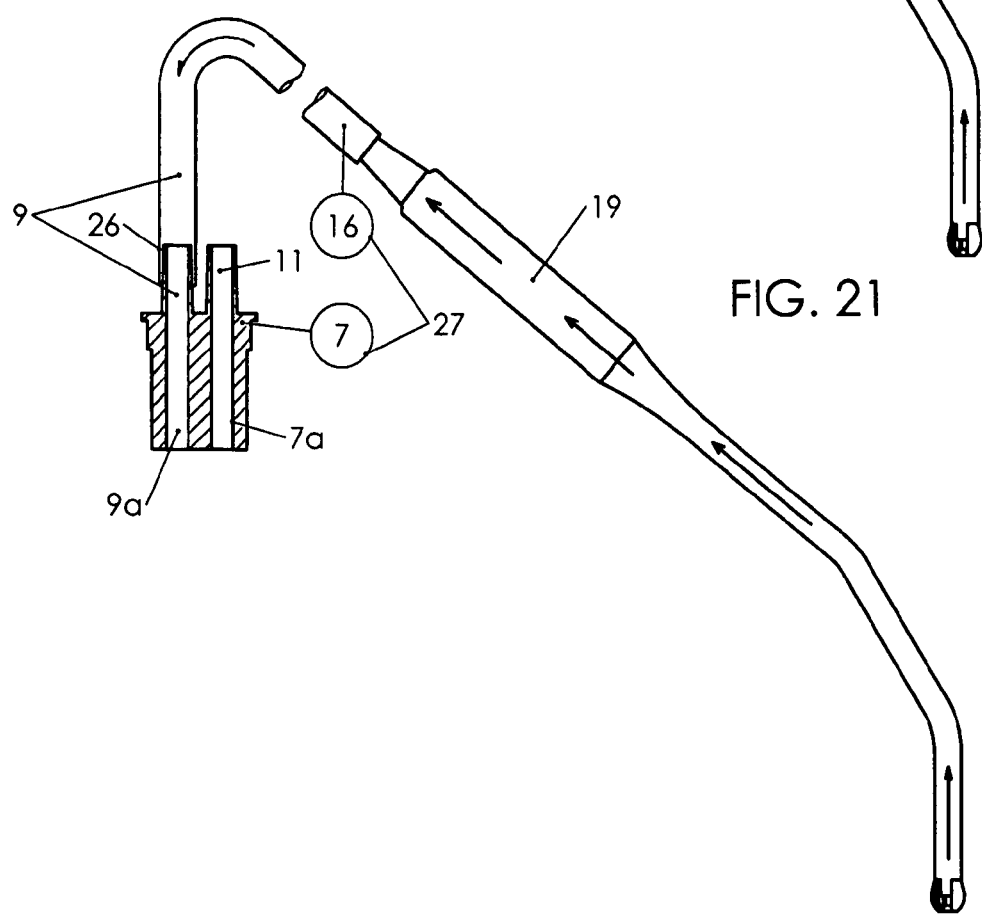
FIG. 21 is a cross sectional view of throat/aperture plug 7a integrally and permanently pre-connected to suction tubing which is in turn connected to a suction tip.

Turning to FIG. 21. FIG. 21 shows material composite conduits of FIG. 19 and FIG. 20 as attached to in-draw connector 9 of a second embodiment throat/aperture plug 7*a*. It is also understood that the in-draw conduit composite of suction tip 19, suction tubing 16 and connector 9 may be permanently joined, or previously releasably connected as an integral material in-draw conduit.

Figure 22:
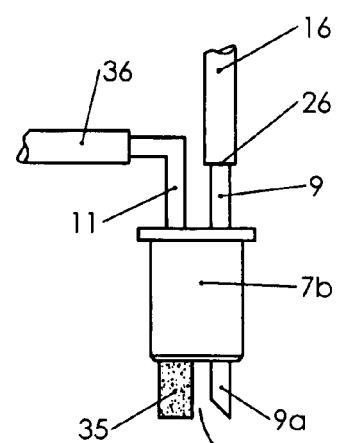
FIG. 22 is a side elevation view of throat/aperture vacuum transfer plug 7b shown as a separate assembly having a filter and separately and releasably connectable to the suction tubing and a vacuum draw line 36 having a filter space.

Turning to FIG. 22. FIG. 22 shows a third embodiment throat/aperture plug 7*b* with out draw line filter 35, out-draw connector 11, outline filter space 36, in-draw connector 9, suction tubing connection 16 and material deposit spout 9*a*. It is understood that these components may be permanently connected to third throat/aperture embodiment 7*b* or they may be releasable connectable to throat/aperture embodiment 7*b*.

Figure 23:
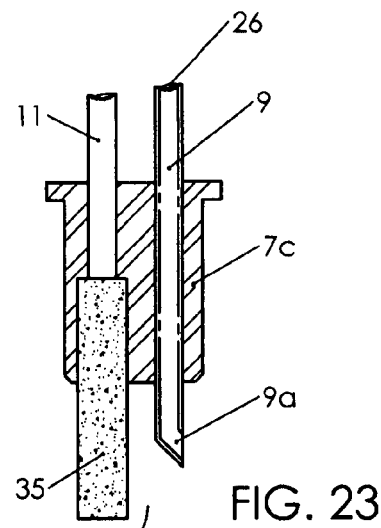

Turning to FIG. 23. FIG. 23 shows a fourth embodiment throat/aperture plug 7*c* having out-draw connector 11, out-draw filter 35 and material in-draw spike (9-9*a*) passageway depicted by 9 through 9*a*. It is understood that material in-draw spike 9 through 9*a* may be permanently assembled/connected to a suction tubing 16 and separable from throat/aperture plug 7*c*.

Figure 24:
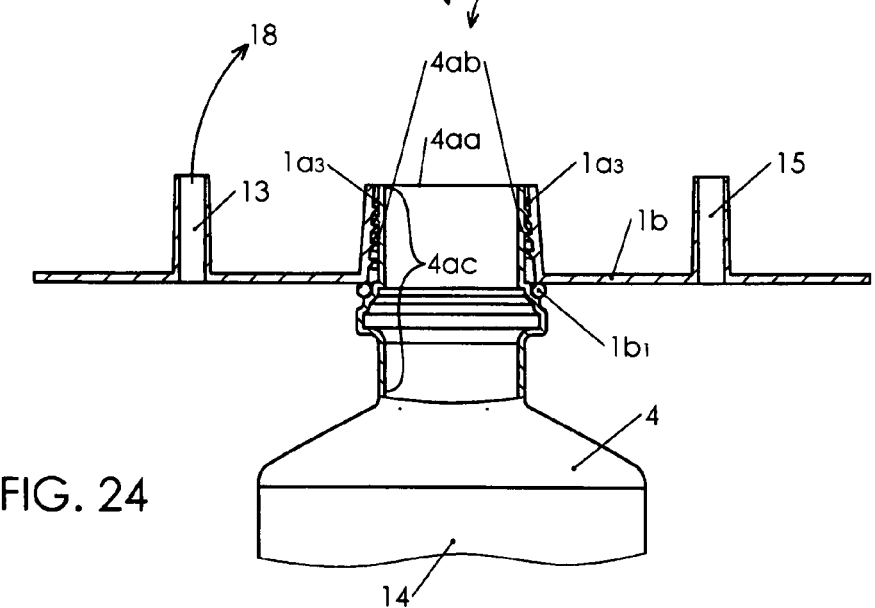
FIG. 24 shows a surgical suction canister lid embodiment 3 1b connected to a plastic pour bottle having an annular O-ring seal disposed to mate with a portion of the pour bottle neck to form a seal.

Turning to FIG. 24. Shows a cross section assembly of plastic pour bottle 4 and third lid embodiment 1*b*. Third lid embodiment 1*b* has similar port connectors 13 and 15, and pour bottle connection threads 4*ab*. Third embodiment lid 1*b* has an O-ring 1*b*1 attached for connection to form a seal with part of pour bottle 4 neck.

Turning to FIG. 25. FIG. 25 shows a material in-draw conduit composite showing suction tip 19, suction tubing 16.

Turning to FIG. 26. FIG. 26 shows a throat/aperture embodiment 7*b* of FIG. 22.

Turning to FIG. 27. FIG. 27 shows a throat/aperture embodiment 7*c* of FIG. 23.

Turning to FIG. 28. FIG. 28 shows a 5$^{th}$ embodiment of throat/aperture plug 7*d* having in-draw spike 9 through 9*a*, outdraw connector 11 and outline filter 35.

Turning to FIG. 29. FIG. 29 shows a fourth lid embodiment 1*c* having a downward annular boss 1*c*1 and lid aperture 1*c*2. Downward lid aperture boss 1*c*1 is sized to fit snugly down the throat 4*aa* of pour bottle 4. Each of the three lines 30, demonstrate that the aperture plugs of FIG. 26, FIG. 27 and FIG. 28 are meant to fit down lid aperture 1*c*2 disposing in-draw spout 9*a* into inner chamber 14 of pour bottle 4 and disposing out draw filters 35 in a position to filter the outdraw. Each of three lines 31 show the connectability of suction tubing 16 to the material in-draw connectors 9 of FIGS. 26, 27 & 28.

Turning to FIG. 30. FIG. 30 shows a second embodiment of a pour bottle 4*c* having peripheral flange 4*ce* formed unitary therewith, locking lug wings 4*ca* and neck throat 4*aa*. FIG. 31 is a cross sectional view of second embodiment of plastic pour bottle 4*c* having internal chamber 14, two locking lug wings 4*ca*, peripheral flange surface 4*cd*, external thread 4*ab* and neck throat 4*aa*.

Turning to FIG. 31. FIG. 31 shows pour bottle 4*c* in position juxtaposed to a partial view of a portion of lid embodiment 1 posed for passage of locking lug wings 4*ca* through slots 1*aa* as depicted in FIG. 2. Locking lug wing under surface 4*cb* is disposed to make contact with lid embodiment 1 ramps 1*ab* for creating a sufficient contact and seal between peripheral flange surface 4*cd* with O-ring 21 as shown in FIG. 7 which is in O-ring groove 1*ac* also shown in FIG. 7. Sub-assembly of FIG. 31 may then be disposed for position with surgical suction canister system as shown by offset line 37. FIGS. 32, 33, 34, and 35 show the throat aperture plugs of FIGS. 23, 22, 21 and 17 respectively. FIG. 36 shows a suction tip 19 and suction tubing 16 as a composite material in-draw line. Each of four lines 32 demonstrate the connectability and/or permanent connection of suction tubing 16 with connection ports 9 and/or spike 9 through 9*a* (of FIG. 27) and with throat/aperture plugs of FIGS. 32, 33, 34 & 35.

Turning to FIG. 37. FIG. 37 shows a cross sectional view of second embodiment pour bottle 4*c* disposed for insertion in connection with lid embodiment 1. Each of four lines 33 demonstrate the direction of connectability between pour bottle 4*c* and each of throat/aperture plugs 7*c*, 7*b*, 7*d* & 7. Sheet 19 of 19 is intended to demonstrate the composite in-draw line connectability forming communication between a suction tip 19 (source of waste material) and the inner chamber 14 of a plastic pour bottle 4*c*. As various changes could be made in the above methods and apparatus without departing from the scope of the invention, and because it is intended that all matter contained in the above description or shown in the accompanying drawings shall be interpreted as illustrative and not in a limiting sense, we therefore claim the aforementioned matter in all forms and combinations limited solely by the appended claims.

What is claimed is:

1. A supply chain method comprising,
   a) providing an aseptic/sterile fluid enclosing container manufactured having its structure characterized by, an axial centerline extending through the center of the top to the center of the base of said container defining a datum reference for structuring a supply chain apparatus in order to seal a vacuum draw path, said container having a predetermined volumetric capacity and weight for transferring an aseptic/sterile fluid, a top defining a pour spout opening having a perimeter, a threaded neck extending downwardly away from said top and forming into an outwardly extending sealing surface, a throat/aperture space defining an egress/ingress opening confined within said container neck, a container cap/closure having threads which correspond to said threads of said container neck, a body extending downwardly and outwardly from said sealing surface to said base and forming substantially said volumetric container capacity to hold said predetermined volume of said aseptic/sterile fluid, an upwardly facing flange seal interposed between said container threads and said container body being defined with a sealing surface, and a container height being defined in aggregate a combination of distances along said axial centerline from said top to said thread, said thread to said seal, said seal to said body and said body to said base,
   b) distributing said aseptic/sterile fluid in said container,
   c) uncapping said container and egressing aseptic/sterile fluid,
   d) threadably connecting said container to the lid of a canister system for consumption against generating garbage/waste in conjunction with collecting fluent waste material under a remotely emanating vacuum draw force,
   e) drawing fluent waste material into said container,
   f) disconnecting said container from said canister lid,
   g) recapping said container with said container cap,
   h) removing said fluent waste material in said container.

2. An apparatus in accordance with the supply chain method of claim 1 comprising,
   a) means for sealing a vacuum draw path.

3. An apparatus of claim 2 further comprising,
   a) means for unsealing said vacuum draw path.

4. A supply chain method of claim 3 wherein said container is provided blow mold manufactured for said supply chain container conversion.

5. A supply chain method of claim 3 wherein said container is provided blow fill seal manufactured for said supply chain container conversion.

6. A supply chain method comprising,
   a) providing an aseptic/sterile liquid said liquid sealed in a container at manufacturing said manufacturing being adapted to provide a predetermined sterility assurance level said container being adapted to be filled and sealed for enclosing said liquid in said container said containing having a neck portion, said neck portion to include an outwardly extending surface, said surface being adapted to provide a sealed connection, said container being adapted to provide said liquid for consumption said seal being adapted to be unsealed to allow egress of said liquid from said container by pouring,
   b) establishing a supplies conversion said container being adapted to be disassociated from said consumption said container being adapted to be converted to provide a sealed vacuum draw path said draw path being adapted to seal vacuum forces between a vacuum and an open end sealed path said forces being adapted to be drawn into and out of a neck portion of said container said container interposed between said vacuum and said open end said path being adapted to exchange draw forces through said neck portion said container being adapted to receive fluent waste material said material drawn by said forces said forces being adapted to be contained along said path, said path to include integration with a waste collection system, said container being adapted to be connected with said system, said system to include said forces, said system to include said path, said system to include at least a container portion, said portion being adapted to be disposed within said path,
   c) unsealing said path by disconnecting said container from said draw path said container being adapted to be resealed for containment and disposal and transfer of fluent waste material said container being adapted to be recycled.

7. A method of claim 6 further comprising,
   a) manufacturing an aseptic/sterile liquid and providing said liquid in a container having a predetermined sterility assurance level,
   b) consuming said liquid,
   c) consuming said container by integration with waste collection system against discarding said container into the garbage said container consumption providing said supplies container conversion for said container to be adapted to collect of fluent waste material,
   c) providing further consumption of said container by removing and transferring fluent waste material in said container,
   d) emptying said container of said fluent waste material by consumption of said container for disposing of said waste material.

8. An apparatus in accordance with the supply chain method of claim 7 comprising,
   a) means for sealing said vacuum draw path.

9. An apparatus of claim 8 further comprising,
   a) means for unsealing said vacuum draw path.

10. An apparatus in accordance with the supply chain method of claim 6 comprising,
    a) means for sealing a vacuum draw path.

11. An apparatus in accordance with the supply chain method of claim 10 comprising,
    a) means for unsealing a vacuum draw path.

12. A supply chain method of claim 7 wherein said container is provided blow mold manufactured for said supply chain container conversion.

13. A supply chain method of claim 7 wherein said container is provided blow fill seal manufactured for said supply chain container conversion.

14. A supply chain method comprising,
    a) providing a waste collection and disposal container said container manufactured having an aseptic/sterile liquid therein hermetically sealed to a predetermined sterility assurance level said container having a neck, said neck being adapted to include an outwardly extending surface, said neck being adapted to provide a seal connection, said container being adapted to be unsealed for consumption egress said aseptic/sterile liquid intended for egressing use related with said consumption,
    b) establishing a supplies waste container conversion said container being adapted to be disassociated from said consumption said container conversion provided in preparation for fluent waste material ingress utility said container being adapted to seal a vacuum draw path said draw path being adapted to seal vacuum draw forces said forces being adapted to be drawn between a vacuum and an open draw path inlet said container being interposed between said inlet and said vacuum said forces being adapted to be drawn away form and toward said container said seal being adapted to provide said path to direct said forces and said waste materials from said inlet toward said vacuum said seal being adapted to draw said vacuum forces and said material toward said container said vacuum being adapted to provide material ingress into said waste collection container said draw forces being adapted to be provided by said vacuum along said path, said forces being adapted to be contained;

c) resealing said waste container for containment of said waste material said container being adapted to be removed and transferred for disposal of said waste material said container being adapted to be separated from said waste material said container being adapted for recycling.

15. A supply chain method of claim 14 comprising,
a) applying said waste container conversion after consumption of said liquid by integration of said container into a waste collection system.

16. A supply chain method of claim 14 further comprising,
a) providing said aseptic/sterile liquid in a supply chain container,
b) providing said container conversion from a supply container to a collection and disposal container,
c) providing said container for waste collection and transport in a disposal chain.

17. A supply chain method of claim 16 further comprising,
a) said converting said container from a supply container to a disposal container in a supply and disposal chain,
b) providing said container conversion.

18. A supply chain method of claim 17 further comprising,
a) providing conversion consumption of a fluent material transfer container from the clean supply side of a supply and disposal chain to the dirty disposal side of said supply and disposal chain.

19. A supply chain method of claim 18 further comprising,
a) utilizing delivery containers for the delivery of an aseptic/sterile material and for the collection of fluent waste material against separately producing collection containers thereby reducing the amount of separate collection container trash contributed into the waste stream as garbage and deferring the disposal of delivery containers into the trash by further fluent waste material collection utility with respect to said delivery containers defining container conversion methods reducing the procurement of said separately produced collection containers thereby reducing associated waste and reducing associated collection container supply chain costs providing said supply chain efficient container conversion method instead of collecting fluent waste materials in said separately produced collection containers.

20. A supply chain method of claim 19 further comprising,
a) extending the useful life of delivery containers.

21. A supply chain method of claim 20 further comprising,
a) reducing fluent waste material collection container waste and associated supply chain costs by extending the useful life of delivery containers from distribution utility to disposal utility.

22. A supply chain method of claim 21 further comprising,
a) manufacturing said delivery container(s) from biodegradable blow moldable materials.

23. A supply chain method of claim 22 further comprising,
a) manufacturing said delivery container(s) from recyclable blow moldable materials.

24. An apparatus in accordance with the supply chain method of claim 18 comprising,
a) means for sealing a vacuum draw path.

25. An apparatus of claim 24 further comprising,
b) means for unsealing a vacuum draw path.

26. A supply chain method of claim 21 wherein said container is provided blow mold manufactured for said supply chain container conversion.

27. A supply chain method of claim 21 wherein said container is provided blow fill seal manufactured for said supply chain container conversion.

* * * * *

UNITED STATES PATENT AND TRADEMARK OFFICE
CERTIFICATE OF CORRECTION

PATENT NO. : 7,329,250 B2　　　　　　　　　　　　　　　　　　　　Page 1 of 1
APPLICATION NO. : 10/730297
DATED : February 12, 2008
INVENTOR(S) : Jack W. Romano and Adam L. Smith It is certified that error appears in the above-identified patent and that said Letters Patent is hereby corrected as shown below:

Col. 4, line 43, delete "a" after "as."(last word (article of line 43).
Col. 5, line 48, delete "the" (between "outside" and "which") to read --outside, which--.
Col. 7, line 61, insert --to-- (between "is" and "which") to read --is to deposit.--
Col. 8, line 3, add --.-- (a period) to the end of line 3.
Col. 9, line 20, add a space -- -- between "a" and "plastic" to read --a plastic.--
Col. 11, line 2, add a space -- -- between "Fig. 3" and "Fig. 4" to clearly begin sentence with Fig. 4…
Col. 11, line 8, add a space -- -- between "Fig. 5" and "Fig. 5" to clearly begin sentence with Fig. 5…..
Col. 11, line 18, delete "is" between "4ac" and "engages" to read --4ac engages--.
Col. 12, line 4, replace "trop" with --top-- to read --a top view--.
Col. 13, line 59, replace "reasonable" with --reasonably--, to read --be reasonably connectable--.
col. 15, line 57, replace "containing" with --container--, to read --container having--.
Col. 15, line 59, replace "sealed" with --seal--, to read --a seal conection--.
Col. 16, line 26, add --a-- between "with" and "waste" to read --with a waste--.
Col. 17, line 15, delete ";" after "contained" and add the phrase --along said path said path to include integration with a waste collection system said container being adapted to be connected with siad system said system to include said forces said system to include said path said system to include at least a container portion said portion being adapted to be disposed within said path,--

Signed and Sealed this

Third Day of June, 2008

JON W. DUDAS
*Director of the United States Patent and Trademark Office*